United States Patent [19]

Noguchi et al.

[11] Patent Number: 5,223,487
[45] Date of Patent: Jun. 29, 1993

[54] PEPTIDES AS ANTIALLERGIC AGENTS

[75] Inventors: Keiichi Noguchi; Noriya Ohta; Daisuke Irie; Katsurou Matsuo; Kouhei Hirano; Asako Tokunaga, all of Hitachi; Fumio Ishikawa, Ichikawa, all of Japan

[73] Assignee: Hitachi Chemical Co., Ltd., Tokyo, Japan

[21] Appl. No.: 824,589

[22] Filed: Jan. 23, 1992

Related U.S. Application Data

[62] Division of Ser. No. 587,967, Sep. 25, 1990, Pat. No. 5,118,669.

[30] Foreign Application Priority Data

| Sep. 30, 1989 | [JP] | Japan | 1-256871 |
| Sep. 30, 1989 | [JP] | Japan | 1-256872 |
| Oct. 3, 1989 | [JP] | Japan | 1-258366 |
| Oct. 3, 1989 | [JP] | Japan | 1-258367 |
| Feb. 26, 1990 | [JP] | Japan | 2-45041 |
| Feb. 26, 1990 | [JP] | Japan | 2-45042 |
| Feb. 26, 1990 | [JP] | Japan | 2-45043 |
| Feb. 27, 1990 | [JP] | Japan | 2-46855 |

[51] Int. Cl.⁵ .................. A61K 37/00; A61K 37/02; C07K 5/00; C07K 7/00
[52] U.S. Cl. ........................ 514/18; 514/17; 530/329; 530/330; 530/331
[58] Field of Search ............ 514/17, 18; 530/329, 530/330, 331

[56] References Cited

U.S. PATENT DOCUMENTS

| 4,161,522 | 7/1979 | Hamburger | 524/177 |
| 4,171,299 | 10/1979 | Hamburger | 530/330 |
| 4,628,045 | 12/1986 | Hahn | 514/17 |
| 4,816,449 | 3/1989 | Hahn | 514/17 |
| 5,118,669 | 6/1992 | Noguchi et al. | 514/17 |

*Primary Examiner*—Lester L. Lee
*Assistant Examiner*—A. M. Davenport
*Attorney, Agent, or Firm*—Abelman Frayne & Schwab

[57] ABSTRACT

The following oligopeptides containing -Asp-Gly- or -Asp-Ser- are synthesized:
H-Asp-Gly-Lys-OH
H-Ser-Asp-Gly-Lys-OH
H-Asp-Ser-Asp-Gly-Lys-OH
H-Ala-Asp-Ser-Asp-Gly-Lys-OH The oligopeptides have antiallergic, vasodilating and immunoregulating activities and are very useful for treating allergic symptoms.

3 Claims, 14 Drawing Sheets

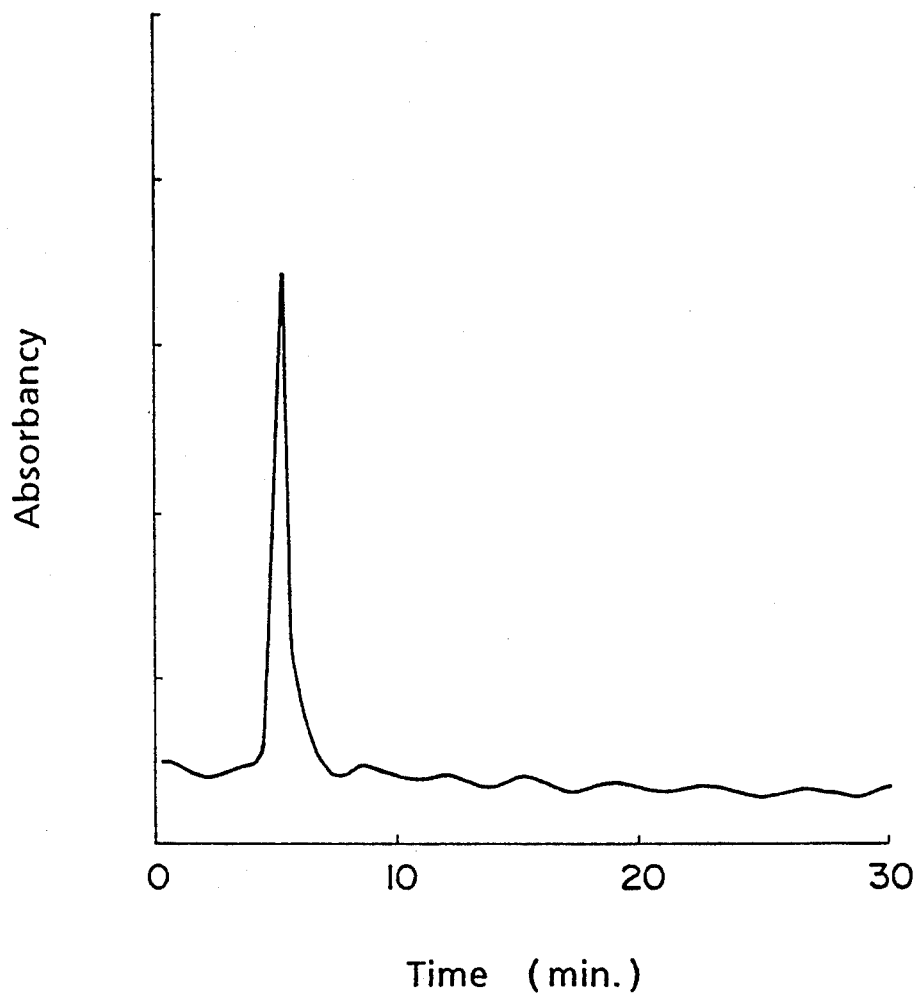
F I G. 1

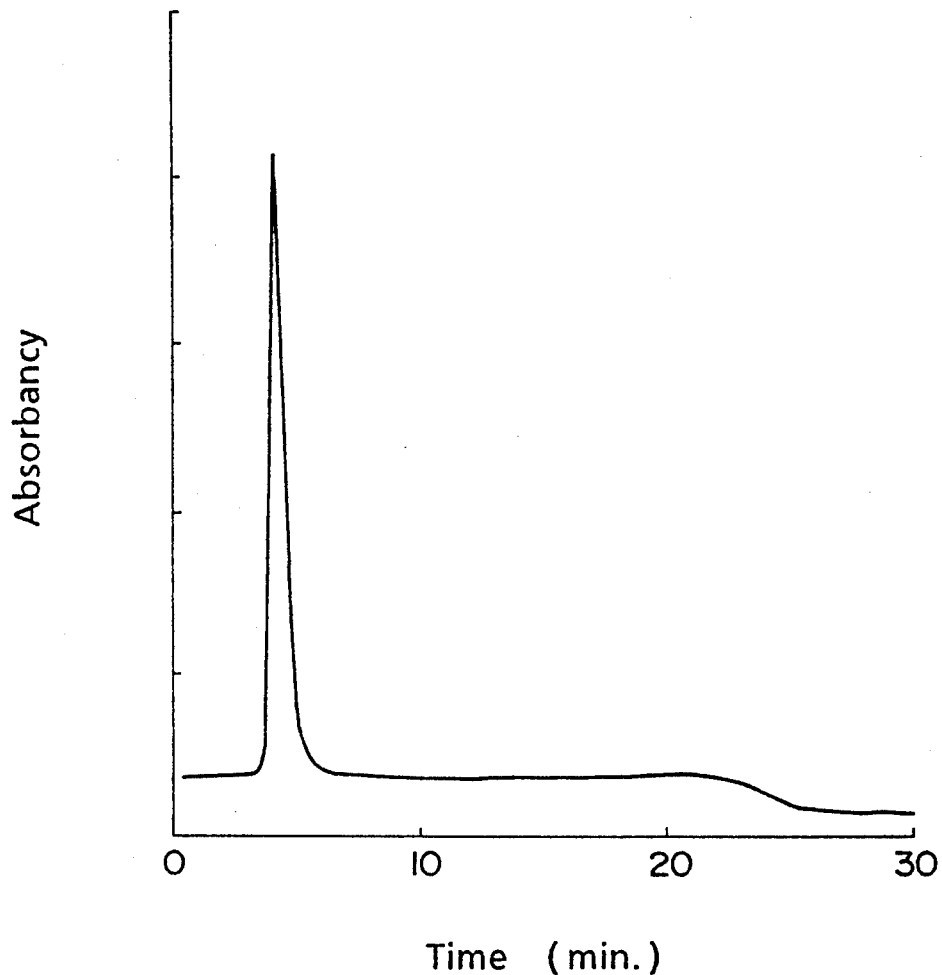
F I G. 2

REPTIDES AS ANTIALLERGIC AGENTS

This is a division of application Ser. No. 587,967 filed on Sep. 25, 1990 and now U.S. Pat. No. 5,118,669.

BACKGROUND OF THE INVENTION

1. Field of the Invention

This invention relates to novel peptides, intermediates therefor, process for preparing the same, and antiallergic agents, vasodilators and immunoregulators.

2. Description of Prior Art

A variety of drugs have been proposed and developed for the prevention or therapy of various allergic diseases. Some of them have already been placed on the market.

Among the allergic symptoms, immediate-type allergic reactions such as bronchial asthma, urticaria and allergic rhinitis are classified as type I-allergic reaction. The type I-allergic reaction is in general believed on the basis of onset of the symptoms and action mechanism of the antiallergic agent to involve the following three stages: First, interaction among macrophage, T cell and B cell against an extraneous antigen which has entered the body produces IgE antibody, which is fixed to the Fc receptor in tissue mast cells or blood basophils thereby producing sensitization (this process is at the first stage; next, when the extraneous antigen again enters the body, the IgE antibody fixed to the Fc receptor in the cells and the extraneous antigen are bonded to cause antigen-antibody reaction which triggers such reactions as activation of the cell membrane enzymes and inflow of calcium ions into cells thereby producing biochemical changes such as enzymatic reactions and histological changes such as degranulation with a result that chemical mediators such as histamine and SRS-A are released outside the cells (this process is at the second stage); the chemical mediators released outside the cells at the second stage have such actions as contraction of smooth muscles and accentuation of permeability and promotion of excretion of the capillary blood vessels and cause various allergic symptoms (this process is at the third stage).

Known antiallergic agents include those for nonspecific hyposensitization therapy as well as for inhibition of antibody production, which are durgs acting on the first stage. None of the drugs specifically acting on the first stage only has been placed on the market. As drugs acting on the second stage are known chemical mediator-inhibitory agents such as disodium cromoglycate (called cromoglycate for short hereinbelow) and Tranilast. Antihistaminics and bronchodilators are drugs acting on the third stage.

Furthermore, there are disclosed antiallergic peptides in U.S. Pat. No. 4,171,299. In the specification is included an IgE antibody-originated pentapeptide composed of five amino acid residues of the Fc portion of IgE antibody as represented by the primary structure H-Asp-Ser-Asp-Pro-Arg-OH.

Inhibition of the IgE antibody production by the peptide has not been confirmed. However, it is believed that the peptide blocks allergic reaction by inhibiting binding of the IgE antibody with mast cells which occurs at the beginning of the second stage, as well as by simultaneously substituting the bound IgE antibody already formed at the second stage with the peptide.

Development of antiallergic agents has heretofore been directed to a drug acting on one of the three stages for the onset of allergic symptoms. Studies were made of prevention of onset or therapeutic treatment of allergic symptoms by blocking at any one stage in the chain of the three stages. Therapy which is expected to produce some efficacy has been developed by such approach.

These known chemotherapeutic agents, however, cannot completely block the chain of the above-mentioned three stages. Consequently, use of a combination of several drugs has been adopted based on an idea of realizing complete blocking of the chain by combined use of a drug acting on one of the three stages with a drug acting on another, but the results are not as expected.

Then, it is expected that development of a single drug acting on plural stages of the three stages in the onset of allergic symptoms would enhance the effects as an antiallergic agent, and development of such drugs is desirable.

It is also conceivable on the basis of mechanism of the onset of allergic symptoms that superior antiallergic agents would become available if a peptide of the Fc portion of IgE antibody origin or a peptide analogous to such peptide is developed. Development of novel peptides by such approach is also expected.

It is an object of this invention to provide antiallergic peptides with superior pharmacological activities by preparing a peptide of the Fc portion of IgE antibody or a peptide analogous thereto.

SUMMARY OF THE INVENTION

In order to achieve the above object and in consideration of the peptides occurring in the Fc portion of IgE antibody we have found a process for preparing peptides containing -Asp-Gly- or -Asp-Ser- or derivatives thereof in a high yield while preventing side reactions. It has been difficult to carry out the process in liquid phase. Various oligopeptides containing an -Asp-Gly- or -Asp-Ser- bond have been synthesized and tested for their antiallergic activities. We have discovered from the test results that peptides represented by the formulae H-Asp-Gly-Lys-OH, H-Ser-Asp-Gly-Lys-OH, H-Asp-Ser-Asp-Gly-Lys-OH and H-Ala-Asp-Ser-Asp-Gly-Lys-OH inhibit not only histamine liberation but also IgE antibody production.

Thus, this invention is concerned with (1) a tetrapeptide represented by the formula H-Ser-Asp-Gly-Lys-OH or a pharmaceutically acceptable salt thereof;

(2) a hexa peptide represented by the formula H-Ala-Asp-Ser-Asp-Gly-Lys-OH or a pharmaceutically acceptable salt thereof;

(3) an aspartic acid-glycine-lysine derivative represented by the formula Z-Asp(OBzl)-Gly-Lys(Z)-OBzl;

(4) a serine-aspartic acid-glycine-lysine derivative represented by the formula Z-Ser(OBzl)-Gly-Lys(Z)-OBzl;

(5) an aspartic acid-serine-aspartic acid-glycine-lysine derivative represented by the formula Z-Asp(OBzl)-Ser-Asp(OBzl)-Gly-Lys(Z)-OBzl;

(6) an alanine-aspartic acid-serine-aspartic acid-glycine-lysine derivative represented by the formula Z-Ala-Asp(OBzl)-Ser-Asp(OBzl)-Gly-Lys(Z)-OBzl;

(7) an aspartic acid-glycine-lysine derivative represented by the formula Boc-Asp(OBzl)-Gly-Lys(Z)-OBzl;

(8) a serine-aspartic acid-glycine-lysine derivative represented by the formula Box-Ser-Asp(OBzl)-Gly-Lys(Z)-OBzl;

(9) an aspartic acid-serine-aspartic acid-glycine-lysine derivative represented by the formula Boc-Asp(OBzl)-Ser-Asp(OBzl)-Gly-Lys(Z)-OBzl;

(10) a process for preparing the peptide H-Asp-Gly-Lys-OH which comprises catalytically reducing the peptide derivative Z-Asp(OBzl)-Gly-Lys(Z)-OBzl according to item (3);

(11) a process for preparing the peptide H-Ser-Asp-Gly-Lys-OH which comprises catalytically reducing the peptide derivative Z-Ser-Asp-(OBzl)-Gly-Lys(Z)-OBzl according to item (4);

(12) a process for preparing the peptide H-Asp-Ser-Asp-Gly-Lys-OH which comprises catalytically reducing the peptide derivative Z-Asp(OBzl)-Ser-Asp(OBzl)-Gly-Lys(Z)-OBzl according to item (5);

(13) a process for preparing the peptide H-Ala-Asp-Ser-Asp-Gly-Lys-OH which comprises catalytically reducing the peptide derivative Z-Ala-Asp(OBzl)-Ser-Asp(OBzl)-Gly-Lys(Z)-OBzl according to time (6);

(14) a process for preparing the peptide derivative Boc-Asp(OBzl)-Gly-Lys(Z)-OBzl which comprises treating a glycine-lysine derivative represented by the formula Boc-Gly-Lys(Z)-OBzl with an acid to eliminate the group Boc followed by addition of an aspartic acid derivative represented by the formula Boc-Asp(OBzl)-OH and subjecting the two to dehydrate condensation;

(15) a process for preparing the peptide derivative Boc-Ser-Asp(OBzl)-Gly-Lys(Z)-OBzl which comprises treating the peptide derivative Boc-Asp(OBzl)-Gly-Lys(Z)-OBzl according to item (7) with an acid to eliminate the group Boc followed by addition of a serine derivative represented by the formula Boc-Ser-OH and subjecting the two to dehydrative condensation;

(16) a process for preparing the peptide derivative Boc-Asp(OBzl)-Ser-Asp(OBzl)-Gly-Lys(Z)-OBzl which comprises treating the peptide derivative Boc-Ser-Asp(OBzl)-Gly-Lys(Z)-OBzl according to item (8) with an acid to eliminate the group Boc followed by addition of an aspartic acid derivative represented by the formula Boc-Asp(OBzl)-OH and subjecting the two to dehydrative condensation;

(17) a process for preparing the peptide derivative Z-Asp(OBzl)-Gly-Lys(Z)-OBzl which comprises treating a glycine-lysine derivative represented by the formula Boc-Gly-Lys(Z)-OBzl with an acid to eliminate the group Boc followed by addition of an aspartic acid derivative represented by the formula Z-Asp(OBzl)-OH and subjecting the two to dehydrative condensation;

(18) a process for preparing the peptide derivative Z-Ser-Asp(OBzl)-Gly-Lys(Z)-OBzl which comprises treating the peptide derivative Boc-Asp(OBzl)-Gly-Lys(Z)-OBzl according to item (7) with an acid to eliminate the group Boc followed by addition of a L-serine derivative represented by the formula Z-Ser-OH and subjecting the two to dehydrative condensation;

(19) a process for preparing the peptide derivative Z-Asp(OBzl)-Ser-Asp(OBzl)-Gly-Lys(Z)-OBzl which comprises treating the peptide derivative Boc-Asp(OBzl)-Gly-Lys(Z)-OBzl according to item (8) with an acid to eliminate the group Boc followed by addition of a serine derivative represented by the formula Boc-Ser-OH and subjecting the two to dehydrative condensation;

(20) a process for preparing the peptide derivative Z-Ala-Asp(OBzl)-Ser Asp(OBzl)-Gly-Lys(Z)-OBzl which comprises treating the peptide derivative Boc-Asp(OBzl)-Ser-Asp(OBzl)-Gly-Lys(Z)-OBzl according to item (9) with an acid to eliminate the group Boc followed by addition of an alanine derivative represented by the formula Z-Ala-OH and subjecting the two to dehydrative condensation;

(21) an antiallergic agent comprising a tripeptide represented by the formula H-Asp-Gly-Lys-OH or a pharmaceutically acceptable salt thereof as an active ingredient;

(22) an antiallergic agent comprising the tetrapeptide or the pharmaceutically acceptable salt thereof according to item (1) as an active ingredient; and

(23) an antiallergic agent comprising the hexapeptide or the pharmaceutically acceptable salt thereof according to item (2) as an active ingredient.

Furthermore, as a result of extensive studies on pharmacological activities of the aforementioned peptides we have unexpectedly found that they have a vasodilator activity and an immunoregulator activity, too.

Thus, the invention relates to (24) a vasodilator comprising a tripeptide represented by the formula H-Asp-Gly-Lys-OH or a pharmaceutically acceptable salt thereof as an active ingredient;

(25) a vasodilator comprising the tetrapeptide or the pharmaceutically acceptable salt thereof according to item (1) as an active ingredient;

(26) a vasodilator comprising a pentapeptide represented by the formula H-Asp-Ser-Asp-Gly-Lys-OH or a pharmaceutically acceptable salt thereof as an active ingredient;

(27) a vasodilator comprising the hexapeptide or the pharmaceutically acceptable salt thereof according to item (2) as an active ingredient;

(28) an immunoregulator comprising a tripeptide represented by the formula H-Asp-Gly-Lys-OH or a pharmaceutically acceptable salt thereof as an active ingredient;

(29) an immunoregulator comprising the tetrapeptide or the pharmaceutically acceptable salt thereof according to item (1) as an active ingredient;

(30) an immunoregulator comprising a pentapeptide represented by the formula H-Asp-Ser-Asp-Gly-Lys-OH or a pharmaceutically acceptable salt thereof as an active ingredient; and

(31) an immunoregulator comprising the hexapeptide or the pharmaceutically acceptable salt thereof according to item (2) as an active ingredient.

The following abbreviations are used throughout the specification and Claims:

Ala:Alanine residue
Arg:Arginine residue
Asp:spartic acid residue
Gly;Glycine residue
Lys:Lysine residue
Pro:Proline residue
Bzl:Benzyl
Z:Benzyloxycarbonl
Boc:t-Butyloxycarbony
DGK:H-Asp-Gly-Lys-OH
SDGK:H-Ser-Asp-Gly-Lys-OH
DSDGK:H-Asp-Ser-Asp-Gly-Lys-OH
ADSDGK:H-Ala-Asp-Ser-Asp-Gly-Lys-OH
DSDPR:H-Asp-Ser-Asp-Pro-Arg-OH

BRIEF DESCRIPTION OF THE DRAWING

FIG. 1 shows a high performance liquid chromatogram of the peptide H-Asp-Gly-Lys-OH produced by the invention.

FIG. 2 shows a high performance liquid chromatogram of the peptide H-Ser-Asp-Gly-Lys-OH of the invention.

In FIGS. 1-4, the vertical axis represents the intensity of ultraviolet absorption at 220 nm and the horizontal axis represents the elution time (minute).

In FIGS. 5-7, the vertical axis represents percent release of histamine (%) and the horizontal axis represents concentration of the compound (M).

In FIGS. 8-13 respectively, the vertical axis represents antibody titer and the horizontal axis represents compounds and dose thereof (mg/kg). In the figures, the bar with slashed lines indicates antibody titer for the corresponding heat-treated serum.

DETAILED DESCRIPTION OF THE INVENTION

Figure 3:
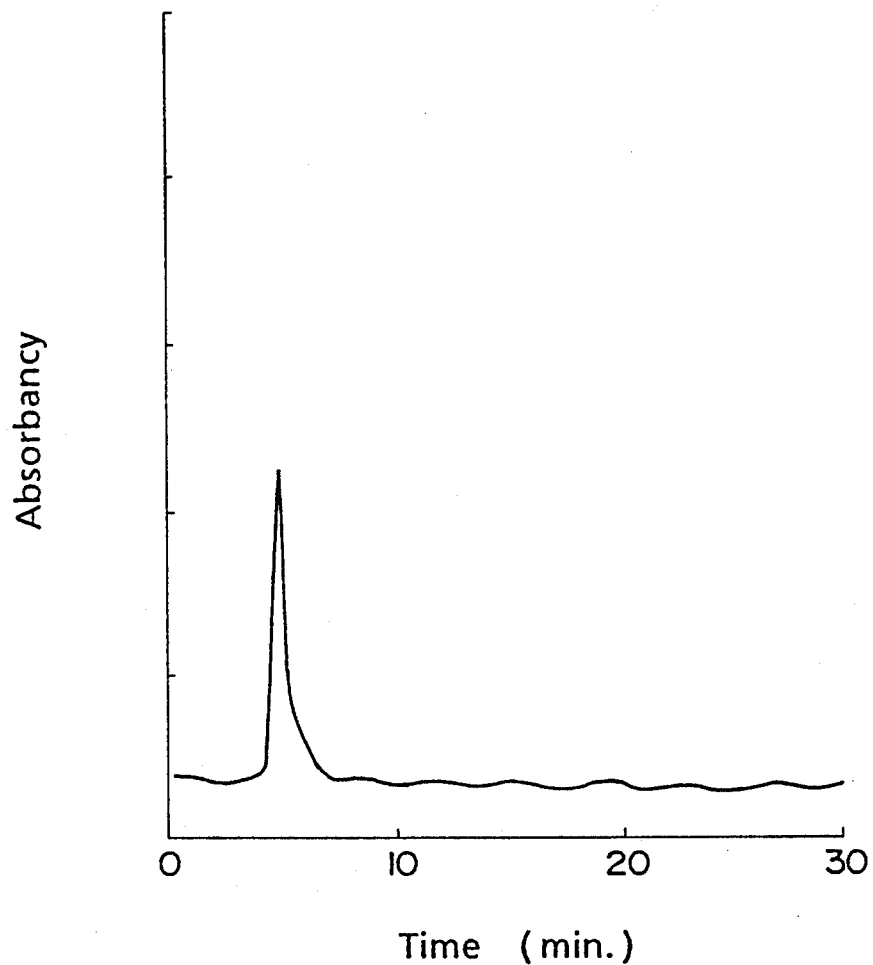
FIG. 3 shows a high performance liquid chromatogram of the peptide H-Asp-Ser-Asp-Gly-Lys-OH produced by the invention.

As pharmaceutically acceptable salts of the peptides of the invention represented by the formula H-Asp-Gly-Lys-Oh, H-Ser-Asp-Gly-Lys-OH, H-asp-Ser-Asp-Gly-Lys-OH or H-Ala-Asp-Ser-Asp-Gly-Lys-OH are mentioned metal salts including salts with an alkali metal such as sodium or potassium and salts with an alkaline earth metal such as calcium or magnesium, ammonium salts, salts with an organic base, salts with an organic acid, salts with an inorganic acid and the like.

The aspartic acid-glycine-lysine derivative of the invention represented by the formula Z-Asp(OBzl)-Gly-Lys(Z)OBzl is an intermediate for a tripeptide represented by the formula H-Asp-Gly-Lys-OH.

The serine-aspartic acid-glycine-lysine derivative of the invention represented by the formula Z-Ser-Asp(OBzl)-Gly-Lys(Z)-OBzl is an intermediate for a tetrapeptide represented by the formula H-Ser-Asp-Gly-Lys-OH.

The aspartic acid-serine-aspartic acid-glycine-lysine derivative of the invention represented by the formula Z-Asp(OBzl)-Ser-Asp(OBzl)-Gly-Lys(Z)-OBzl is an intermediate for a pentapeptide represented by the formula H-Asp-Ser-Asp-Gly-Lys-OH.

The alanine-aspartic acid-serine-aspartic acid-glycine-lysine derivative of the invention represented by the formula Z-Ala-Asp(OBzl)-Ser-Asp(OBzl)-Gly-Lys(Z)-OBzl is an intermediate for a hexapeptide represented by the formula H-Ala-Asp-Ser-Asp-Gly-Lys-OH.

The aspartic acid-glycine-lysine derivative of the invention represented by the formula Boc-Asp(OBzl)-Gly-Lys(Z)-OBzl is an intermediate for a serine-aspartic acid-glycine-lysine derivative represented by the formula Z-Ser-Asp(OBzl)-Gly-Lys(Z)-OBzl.

The serine-aspartic acid-glycine-lysine derivative of the invention represented by the formula Boc-Ser-Asp(OBzl)-Gly-Lys(Z)-OBzl is an intermediate for the peptide derivative Z-Asp(OBzl)-Ser-Asp(OBzl)-Gly-Lys(Z)-OBzl.

The aspartic acid-serine-aspartic acid-glycine-lysine derivative of the invention represented by the formula Boc-Asp(OBzl)-Ser-Asp(OBzl)-Gly-Lys(Z)-OBzl is an intermediate for an alanine-aspartic acid-serine-aspartic acid-glycine-lysine derivative represented by the formula Z-Ala-Asp(OBzl)-Ser-Asp(OBzl)-Gly-Lys(Z)-OBzl.

The tripeptide represented by the formula H-Asp-Gly-Lys-OH can be prepared via Steps 1-4 as shown below.

Step 1:

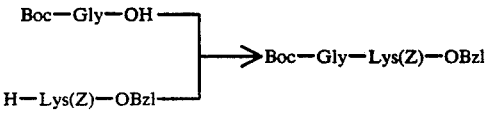

Step 2:

Boc—Gly—Lys(Z)—OBzl ⟶ H—Gly—Lys(Z)—OBzl

Step 3:

-continued

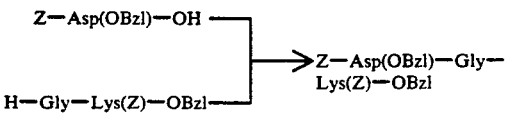

Step 4:

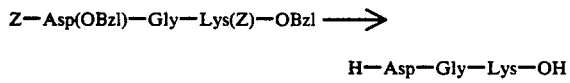

The glycine derivative Boc-Gly-OH wherein the α-amino group is protected by the group Boc and the lysine derivative H-Lys(Z)-OBzl wherein the -carboxyl group protected by the group OBzl and the ε-amino group is protected by the group Z, used in Step 1 are usually the L isomers. The isomers are readily available on the market in free or salt form.

The dehydrative condensation reaction of Boc-Gly-OH and H-Lys(Z)-OBzl can be effected as follows: To a solution of Boc-Gly-OH in a solvent selected from dimethylformamide, tetrahydrofuran, methylene chloride, acetonitrile and the like (which may be a mixed solvent) are added with stirring dicyclohexylcarbodiimide (called DCC hereinbelow) and 1-hydroxybenzotriazole (called HOBt hereinbelow) respectively in an amount of 1.0-1.4 moles per mole of the Boc Gly-OH at or below 0° C., preferably at or below −8° C. followed by addition of an equimolar amount of H-Lys(Z)-OBzl. The mixture is stirred at or below 0° C., preferably at or below −8° C. for 1-10 hours, preferably for 4-6 hours. Stirring is continued at room temperature for additional 1-10 hours, preferably for additional 4-6 hours. The temperature is maintained initially at or below 0° C. in order to prevent formation of by-products (acylureas), and subsequently at room temperature in order to promote formation of the peptide bond.

The by-products formed during the reaction and unreacted starting materials are removed by appropriate procedures such as filtration and washing with an alkali, and the solvent by an operation such as evaporation under reduced pressure. Work up of the product by an operation such as recrystallization affords Boc-Gly-Lys(Z)-OBzl.

As the acid used in Step 2 for the elimination of the group Boc from Boc-Gly-Lys(Z)-OBzl are mentioned trifluoroacetic acid (called TFA hereinbelow), hydrochloric acid, acetic acid, hydrobromic acid, formic acid and the like. A cation scavenger such as anisole, thioanisole, phenol or metacresol may be added together with the acid. A weak acid such as TFA in an amount of 10-30 moles and a cation scavenger such as anisole in an amount of 1-1.3 moles per mole of Boc-Gly-Lys(Z)-OBzl are added, and the mixture is stirred until the group Boc is eliminated. After the reaction, a solvent such as ether or petroleum ether is added to remove the acid and the cation scavenger. Precipitates are collected and dried by an appropriate method such as vacuum drying to give H-Gly-Lys(Z)-OBzl.

The aspartic acid derivative Z-Asp(OBzl)-OH wherein the δ-carboxyl group is protected by Bzl, one of the starting materials used in the reaction in Step 3 is usually the L isomer. It is readily available on the market in free or salt form.

The dehydrative condensation reaction of Z-Asp(OBzl)-OH and H-Gly-Lys(Z) OBzl can be effected as follows: To a solution of Z-Asp(OBzl)-OH in a highly polar solvent such as dimethylformamide are added DCC and HOBt respectively in an amount of 1.0-1.4 moles per mole of the Z-Asp(OBzl)-OH at or below 0° C., preferably at or below −8° C. The mixture is stirred for 1-10 hours, preferably for 4-6 hours followed by addition of a solution of the H-Gly-Lys(Z)-OBzl obtained in Step 2 in an equimolar amount to Z-Asp(OBzl)-OH in a solvent such as dimethylformamide. The resulting mixture is stirred at or below 10° C. for additional 1-24 hours. The reaction is carried out at or below 10° C. in order to prevent a side reaction (formation of an imide) occurring between Asp and Gly.

After completion of the reaction, the by-products and unreacted starting materials are removed in the same way as in Step 1, and Z-Asp(OBzl)-Gly-Lys(Z)-OBzl is obtained after work up by an operation such as recrystallization The Step 4 yields the desired tripeptide H-Asp-Gly-Lys-OH by catalytic reduction of the Z-Asp(OBzl)-Gly-Lys(Z)-OBzl obtained in Step 3 to eliminate the protective groups. The reaction may be achieved by stirring a solution of Z-Asp(OBzl)-Gly-Lys(Z)-OBzl in a solvent such as a mixture of methanol, acetic acid and water in the presence of a catalyst such as palladium black or palladium carried on carbon powders while introducing hydrogen gas.

The tetrapeptide of the invention represented by the formula H-Ser Asp Gly-Lys-OH can be prepared via Steps 1-6 as shown below.

Steps 1 and 2

The same as the above described Steps 1 and 2 for the tripeptide.

Step 3:

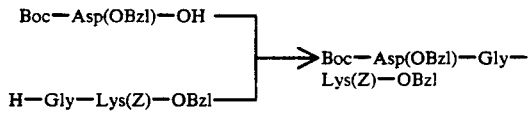

Step 4:

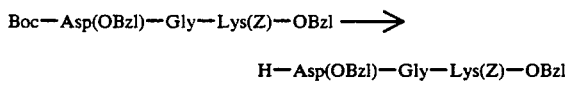

Step 5:

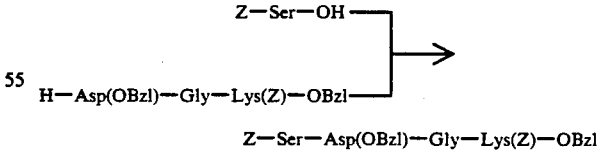

Step 6:

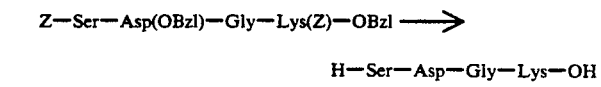

The aspartic acid derivative Boc-Asp(OBzl)-OH wherein the α-amino group is protected by Boc and the β-carboxyl group is protected by Bzl, one of the starting materials used in the reaction in step 3 is usually the L isomer. It is readily available on the market in free or salt form.

The dehydrative condensation reaction of Boc-Asp(OBzl)-OH and H-Gly-Lys(Z)-OBzl can be carried out in the same way as in the dehydrative condensation reaction in step 1.

After completion of the reaction, the by-products and unreacted starting materials are removed in the same way as in Step 1, and Boc-Asp(OBzl)-Gly-Lys(Z)-OBzl is obtained after work up by an operation such as recrystallization.

In Step 4 the Boc-Asp(OBzl)-Gly-Lys(Z)-OBzl obtained in Step 3 is treated under the same conditions as in Step 2 to eliminate the group Boc with an acid.

The serine derivative Z-Ser-OH wherein the α-amino group is protected by the group Z, one of the starting materials used in the reaction in Step 5 is usually the L isomer. It is readily available on the market in free form.

The dehydrative condensation reaction of Z-Ser-OH and H-Asp(OBzl)-Gly-Lys(Z)-OBzl is carried out in the same way as in the dehydrative condensation reaction in Step 2.

The Step 6 yields the desired tetrapeptide H-Ser-Asp-Gly-Lys-OH by catalytic reduction of the Z-Ser-Asp(OBzl)-Gly Lys(Z)-OBzl obtained in Step 5 to eliminate the protective groups. The reaction may be achieved by stirring a solution of Z-Ser-Asp(OBzl)-Gly-Lys(Z)-OBzl in a solvent such as a mixture of methanol, acetic acid and water in the presence of a catalyst such as palladium black or palladium carried on carbon powders while introducing hydrogen gas.

The pentapeptide of the invention represented by the formula H-Asp-Ser-Asp-Gly-Lys-OH can be prepared va Steps 1-8 as shown below.

Steps 1-4

The same as the above-described Steps 1-4 for the tetrapeptide.

Step 5:

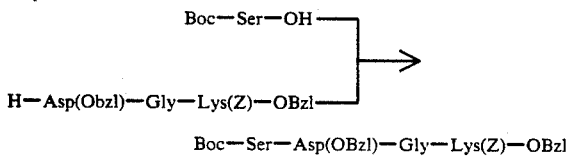

Boc—Ser—Asp(OBzl)—Gly—Lys(Z)—OBzl

Step 6:

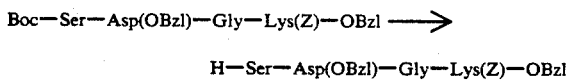

Boc—Ser—Asp(OBzl)—Gly—Lys(Z)—OBzl ⟶

H—Ser—Asp(OBzl)—Gly—Lys(Z)—OBzl

Step 7:

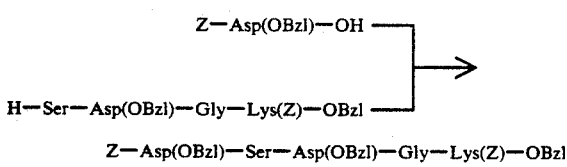

Z—Asp(OBzl)—Ser—Asp(OBzl)—Gly—Lys(Z)—OBzl

Step 8:

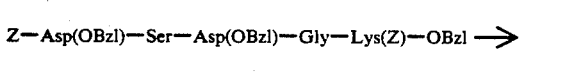

Z—Asp(OBzl)—Ser—Asp(OBzl)—Gly—Lys(Z)—OBzl ⟶

H—Asp—Ser—Asp—Gly—Lys—OH

The serine derivative Boc-Ser-OH wherein the α-amino group is protected by the group Boc, one of the starting materials used in the reaction in Step 5 is usually the L isomer. It is readily available on the market in free form.

The dehydrative condensation reaction of Boc-Ser-OH and H-Asp(OBzl)-Gly-Lys(Z)-OBzl is carried out in the same way as in the dehydrative condensation reaction in Step 1.

In Step 6 the Boc-Ser-Asp(OBzl)-Gly-Lys(Z)-OBzl obtained in Step 5 is treated under the same conditions as in Step 2 to eliminate the group Boc with an acid.

In Step 7 the dehydrative condensation reaction of Z-Asp(OBzl)-OH and H-Ser-Asp(OBzl)-Gly-Lys(Z)-OBzl is carried out under the same conditions as in Step 3.

The Step 8 yields the desired pentapeptide H-Asp-Ser-Asp-Gly-Lys-OH by catalytic reduction of the Z-Asp(OBzl)-Ser-Asp(OBzl)-Gly-Lys(Z)-OBzl obtained in Step 7 to eliminate the protective groups. The reaction may be achieved by stirring a solution of Z-Asp(OBzl)-Ser-Asp(OBzl)-Gly-Lys(Z)-OBzl in a solvent such as a mixture of ethanol, acetic acid and water in the presence of a catalyst such as palladium black or palladium carried on carbon powders while introducing hydrogen gas.

After completion of the reaction, the catalyst is removed by filtration. The filtrate is concentrated under reduced pressure to a small liquid volume. To the residue is added an organic solvent such as ether followed by shaking to remove unreacted starting materials and impurities. The purified peptide is obtained from the aqueous layer by a conventional purification means such as gel chromatography.

Pharmaceutically acceptable salts of H-Asp-Gly-Lys-OH, H-Ser-Asp-Gly-Lys-OH, H-Asp-Ser-Asp-Gly-Lys-OH and H-Ala-Asp-Ser-Asp-Gly-Lys-OH may be prepared by adding a base such as sodium hydroxide or potassium hydroxide or an acid such as hydrochloric acid or acetic acid to a reaction mixture after the elimination of the protective groups in a final preparative step as described above. The conversion to a corresponding salt is thereby resulted. Or, the salts may also be formed by isolating the peptide followed by likewise adding a base or an acid.

Determination of structure and purity of the substances of the present invention is conducted by such means as high performance liquid chromatography, elementary analysis and amino acid analysis.

The antiallergic agent, vasodilator or immunoregulator of the present invention include pharmaceutical preparations comprising the present compound or a medicinally acceptable salt thereof together with pharmaceutically acceptable carriers or diluents. Preferable examples of the salts include salts with an alkali metal such as sodium or potassium and salts with a metal such as an alkali earth metal, for example, calcium or magnesium, ammonium salts, salts with an organic base, salts with an organic acid and salts with an inorganic acid. The present preparations may be formulated so that the active ingredient is released rapidly, continuously or sustainedly following administration to patients.

The antiallergic agent, vasodilator or immunoregulator according to the invention may appropriately be in the form either for oral administration or for parenteral administration. They can be administered by various routes typical of which are oral, rectal, cutaneous, subcutaneous, intravenous, intramuscular, inhalative and nasal ones.

The antiallergic agent, vasodilator or immunoregulator of the invention can be administered in various forms of pharmaceutical preparations by the various routes. As these pharmaceutical preparations are mentioned tablet, hard capsule, soft capsule, granule, powder, troche, suppository, syrup, cream, ointment, cataplasma, injection, suspension, inhalation, aerosol and the like. They may also be formed into bilayer tablet or multilayer tablet together with other antiallergic agents, vasodilator, immunoregulator and other drugs. The tablet can further be coated, as needed, by a conventional method to prepare sugar coated tablet or enteric coating tablet, for example.

In forming solid preparations such as tablet, granule and powder, known additives such as lactose, sucrose, glucose, crystalline cellulose, corn starch, calcium phosphate, sorbitol, glycine, carboxymethyl-cellulose, hydroxypropylcellulose, gum arabic, polyvinylpyrrolidone, polyethylene glycol, magnesium stearate and talc may be added.

In producing semi-solid preparations such additives as vegetable wax, microcrystalline wax and fat, for example, tallow or lanolin may be added.

In preparing liquid preparations such additives as sodium chloride, sorbitol, glycerin, olive oil, almond oil, propylene glycol, and ethylene glycol may be added.

Dosage of the present compound is 0.01-10 mg/kg/day in oral administration, 0.1-100 mg per shot in nasal administration and 10-1,000 µg/kg/day in parenteral administration, although it may appropriately be increased on decreased depending upon age, bodyweight and symptom of the patient.

EXAMPLES

The invention will be described in detail with reference to examples given below.

EXAMPLE 1

Preparation of Z-Asp(OBzl)-Gly-Lys(Z)-OBzl

To a solution of 20.35 g of H-Lys(Z)-OBzl·HCl (manufactured by Kokusan Kagaku) in 35 ml of dimethylformamide (called DMF hereinbelow), after neutralized by addition under cooling with ice of 7 ml of triethylamine, were added 8.76 g of Boc-Gly-OH (manufactured by Kokusan Kagaku), 7.43 g of HOBt (manufactured by Kokusan Kagaku) and 11.35 g of DCC (manufactured by Kokusan Kagaku). The mixture was stirred for 3 hours and at 4° C. for additional 16 hours. Dicyclohexylurea by-product was removed by filtration followed by addition of 300 ml of ethyl acetate. The resulting mixture was washed successively with saturated aqueous sodium chloride, 8% by weight aqueous sodium carbonate, saturated aqueous sodium chloride, 8% by weight aqueous citric acid and saturated aqueous sodium chloride. From the ethyl acetate layer, after dried over anhydrous sodium sulfate, was removed the solvent, and the residue was again dissolved in a small amount of ethyl acetate. From the solution after filtered, the solvent was completely distilled off to give 21.1 g (80% yield) of Boc-Gly-Lys(Z)-OBzl as an oily substance.

To 2.24 g of the Boc-Gly-Lys(Z)-OBzl were added 0.32 g of anisole and 3.24 ml of TFA to give a solution. The solution was stirred at room temperature for one hour to eliminate the group Boc. To the solution was added 100 ml of an ether/petroleum ether mixture (1:1 in volume ratio) to precipitate H-Gly-Lys(Z)-OBzl·TFA. The precipitates were dried by suction in a desiccator containing sodium hydroxide. Separately, 1.50 g of Z-Asp(OBzl)-OH (manufactured by Kokusan Kagaku), 0.62 g of HOBt and 0.95 g of DCC were dissolved in 10 ml of DMF. The solution was stirred under cooling with ice for 3 hours, to which was then added a solution of the above-obtained H-Gly-Lys(Z)OBzl·TFA in 10 ml of DMF containing 0.59 ml of triethylamine. The mixture was stirred overnight at 4° C.

Dicyclohexylurea was removed by filtration followed by addition of ethyl acetate. The mixture was washed successively with 8% by weight aqueous $Na_2CO_3$, saturated aqueous sodium chloride, 0.1N HCl and saturated sodium chloride. The ethyl acetate layer was dried over anhydrous sodium sulfate, and the solvent distilled off. The residue was precipitated from ether and further from ethyl acetate/ether to give 11.17 g (52.3% yield) of Z-Asp(OBzl)-Gly-Lys(Z)-OBzl.

Melting point: 60°–61° C.

$[\alpha]^{26}: -16.3°$ (c=0.93, DMF)

Rf in thin layer chromatography [chloroform/methanol/water (8:3:1 in volume ratio)]: 0.82

Elementary analysis: (for $C_{42}H_{46}N_4O_{10} \cdot \frac{1}{2}H_2O$) (%)

|  | C | H | N |
|---|---|---|---|
| Calc'd: | 65.02 | 6.11 | 7.22 |
| Found: | 65.09 | 6.13 | 7.41 |

Amino acid analysis after acid decomposition: (molar ratio)

| Aspartic acid | 0.9 |
|---|---|
| Glycine | 0.8 |
| Lysine | 1.0 |

EXAMPLE 2

Preparation of H-Asp-Gly-Lys-OH

To a solution of 400 mg of the Z-Asp(OBzl)-Gly-Lys(Z)-OBzl in 20 ml of methanol, 8 ml of acetic acid and 12 ml of water was added 600 mg of 5% Pd-carbon. Into the mixture was introduced hydrogen gas for 5 hours to eliminate all of the protective groups. The Pd-carbon was removed by filtration, and water added to the filtrate. The solvents were distilled off under reduced pressure, and the residue washed with ether. Water was again added to the residue, and the mixture concentrated under reduced pressure to a volume of approximately 2 ml. The concentrate was placed on a Sephadex G-10 column (manufactured by Pharmacia, 2.5×42 cm) and developed with a 0.5% by weight aqueous solution of acetic acid. Fractions each 4 ml in volume were collected, of which fractions the 24–28th showed a single peak. The fractions were pooled and freeze-dried to give 47.1 mg (28% yield) of the tripeptide H-Asp-Gly-Lys-OH.

$[\alpha]_D^{26}: -8.6°$ (c=0.16, $H_2O$)

Rf in thin layer chromatography [n-butanol/pyridine/acetic acid/water (1:1:1:1 in volume ratio)]: 0.63

High performance liquid chromatography: FIG. 1

Elementary analysis: (for $C_{12}H_{22}N_4O_6 \cdot \frac{1}{2}CH_3COOH \cdot 3H_2O$) (%)

|  | C | H | N |
|---|---|---|---|
| Calc'd: | 39.00 | 7.05 | 13.99 |
| Found: | 38.86 | 7.29 | 14.06 |

Amino acid analysis after acid decomposition: (molar ratio)

| Aspartic acid | 1.0 |
|---|---|
| Glycine | 0.9 |
| Lysine | 1.0 |

The high performance liquid chromatography was run in a high performance liquid chromatographic instrument, type M600 manufactured by Waters using as column YMC Pack A-302 ODS (manufactured by Yamamura Kagaku Kenkyusho, 4.×100 mm). A 95:5 (volume ratio) mixture and subsequently a 70:30 (volume ratio) mixture of water containing 0.05% TFA and acetonitrile containing 0.05% TFA were stepwise used as the solvent, and the flow rate was 0.5 ml/min. Detection was made at a wave length of 220 nm.

EXAMPLE 3

Preparation of Boc-Asp(OBzl)-Gly-Lys(Z)-OBzl

To 13.98 g of the Boc-Gly-Lys(Z)-OBzl obtained in Example 1 were added 2 ml of anisole and 20 ml of TFA to give a solution. The solution was stirred at room temperature for one hour to eliminate the group Boc. To the solution was added 80 ml of an ether/petroleum ether mixture (1:1 in volume ratio) to precipitate H-Gly-Lys(Z)-OBzl·TFA. The precipitates were dried by suction in a desiccator containing sodium hydroxide.

Separately, 8.41 g of Boc-Asp(OBzl)-OH (manufactured by Kokusan Kagaku), 3.92 g of HOBt and 5.98 g of DCC were dissolved in 20 ml of DMF. The solution was stirred under cooling with ice for 3 hours, to which was then added a solution of the above-obtained H-Gly-Lys(Z)OBzl·TFA in 15 ml of DMF containing 3.64 ml of triethylamine. The mixture was stirred overnight at 4° C.

Dicyclohexylurea was removed by filtration followed by addition of 400 ml of ethyl acetate. The mixture was washed successively with saturated aqueous sodium chloride, 8% by weight aqueous $Na_2CO_3$, saturated aqueous sodium chloride, 8% by weight aqueous citric acid, saturated sodium chloride and water. The ethyl acetate layer was dried over anhydrous sodium sulfate, and the solvent distilled off. The residue was precipitated from petroleum ether and further reprecipitated from ethyl acetate/petroleum ether to give 14.75 g (76.9% yield) of Boc-Asp(OBzl)-Gly-Lys(Z)-OBzl.

Melting point: 70°-72° C.
$[\alpha]_D^{26}$: −19.0° (c=1.0, DMF)
Rf in thin layer chromatography [chloroform/methanol/water (8:3:1 in volume ratio)]: 0.80
Elementary analysis: (for $C_{39}H_{48}N_4O_{10}·\frac{1}{2}H_2O$) (%)

|  | C | H | N |
|---|---|---|---|
| Calc'd: | 63.14 | 6.66 | 7.55 |
| Found: | 63.13 | 6.64 | 7.72 |

Amino acid analysis after acid decomposition: (molar ratio)

| Aspartic acid | 0.8 |
|---|---|
| Glycine | 0.8 |
| Lysine | 1.0 |

EXAMPLE 4

Preparation of Z-Ser-Asp(OBzl)-Gly-Lys(Z)-OBzl

To 2.40 g of the Boc-Asp(OBzl)-Gly-Lys(Z)-OBzl obtained in Example 3 were added 0.43 ml of anisole and 4.24 ml of TFA to give a solution. The solution was stirred at room temperature for one hour to eliminate the group Boc. To the solution was added 80 ml of an ether/petroleum ether mixture (1:1 in volume ratio) to precipitate H-Asp(OBzl)-Gly-Lys(Z)-OBzl·TFA. The precipitates were dried by suction in a desiccator containing sodium hydroxide.

Separately, 0.84 g of Z-Ser(OBzl)-OH (manufactured by Kokusan Kagaku), 0.54 g of HOBt and 0.83 g of DCC were dissolved in 10 ml of DMF. The solution was stirred under cooling with ice for 3 hours, to which was then added a solution of the above-obtained H-Asp(OBzl)-Gly-Lys(Z)-OBzl·TFA in 10 ml of DMF containing 0.49 ml of triethylamine. The mixture was stirred overnight at 4° C.

Dicyclohexylurea was removed by filtration followed by addition of 200 ml of ethyl acetate. The mixture was washed successively with saturated aqueous sodium chloride, 8% by weight aqueous $Na_2CO_3$, saturated aqueous sodium chloride, 0.1N HCl and saturated sodium chloride The ethyl acetate layer was dried over anhydrous sodium sulfate, and the solvent distilled off. The residue was precipitated from petroleum ether and further reprecipitated from ethyl acetate/petroleum ether to give 1.20 g (43% yield) of Z-Ser-Asp(OBzl)-Gly-Lys(Z)-OBzl.

Melting point: 70°-72° C.
$[\alpha]_D^{26}$: −16.8° (c=0.75, DMF)
Rf in thin layer chromatography [chloroform/methanol/water (8:3:1 in volume ratio)]: 0.83
Elementary analysis: (for $C_{45}H_{51}N_5O_{12}·H_2O$) (%)

|  | C | H | N |
|---|---|---|---|
| Calc'd: | 61.99 | 6.12 | 8.03 |
| Found: | 61.99 | 5.99 | 8.30 |

Amino acid analysis after acid decomposition: (molar ratio)

| Aspartic acid | 0.9 |
|---|---|
| Serine | 1.1 |
| Glycine | 0.8 |
| Lysine | 1.0 |

EXAMPLE 5

Preparation of H-Ser-Asp-Gly-Lys-OH

· To a solution of 400 mg of the Z-Ser-Asp(OBzl)Gly-Lys(Z)-OBzl obtained in Example 4 in 20 ml of methanol, 8 ml of acetic acid and 12 ml of water was added 800 mg of 5% Pd-carbon. Into the mixture was introduced hydrogen gas for 4 hours to eliminate all of the protective groups. The Pd-carbon was removed by filtration, and water added to the filtrate. The solvents were distilled off under reduced pressure, and the residue washed with ether. Water was again added to the residue, and the mixture concentrated under reduced pressure to a volume of approximately 2 ml. The concentrate was placed on a Sephadex G-10 column (manufactured by Pharmacia, 2.5×42 cm) and developed with a 0.5% by weight aqueous solution of acetic acid. Fractions each 4 ml in volume were collected, of which fractions 24–29 showed a single peak. The fractions were pooled and freeze-dried to give 60.8 mg (32% yield) of the tetrapeptide H-Ser-Asp-Gly-Lys-OH.

$[\alpha]_D^{26}$: −8.6° (c=0.16, H$_2$O)

Rf in thin layer chromatography [n-butanol/pyridine/acetic acid/water (1:1:1:1 in volume ratio) ]: 0.53

High performance liquid chromatography: FIG. 2

Elementary Analysis: (for $C_{15}H_{17}N_5O_8 \cdot \frac{1}{2}CH_3COOH \cdot 3H_2O$) (%)

|  | C | H | N |
|---|---|---|---|
| Calc'd: | 38.71 | 7.31 | 14.14 |
| Found: | 38.80 | 7.13 | 14.12 |

Amino acid analysis after acid decomposition: (molar ratio)

| Aspartic acid | 0.9 |
|---|---|
| Serine | 0.9 |
| Glycine | 0.8 |
| Lysine | 1.0 |

EXAMPLE 6

Preparation of Boc-Ser-Asp(OBzl)-Gly-Lys(Z)-OBzl

To 10.0 g of the Boc-Asp(OBzl)-Gly-Lys(Z)-OBzl were added 2 ml of anisole and 20 ml of TFA to give a solution. The solution was stirred at room temperature for one hour to eliminate the group Boc. To the solution was added 150 ml of an ether/petroleum ether mixture (1:2 in volume ratio) to precipitate H-Asp(OBzl)-Gly-Lys(Z)-OBzl·TFA. The precipitates were dried by suction in a desiccator containing sodium hydroxide.

Separately, 2.87 g of Boc-Ser-OH (manufactured by Kokusan Kagaku), 2.16 g of HOBt and 3.30 g of DCC were dissolved in 20 ml of DMF. The solution was stirred under cooling with ice for 3 hours, to which was then added a solution of the above-obtained H-Asp(OBzl)-Gly-Lys(Z)-OBzl·TFA in 20 ml of DMF containing 1.96 ml of triethylamine. The mixture was stirred overnight at 4° C.

Dicyclohexylurea was removed by filtration followed by addition of 300 ml of ethyl acetate. The mixture was washed successively with saturated aqueous sodium chloride, 8% by weight aqueous Na$_2$CO$_3$, saturated aqueous sodium chloride, 8% by weight aqueous citric acid, and saturated sodium chloride. The ethyl acetate layer was dried over anhydrous sodium sulfate, and the solvent distilled off. The residue was precipitated from petroleum ether and further reprecipitated from ethyl acetate/petroleum ether to give 5.83 g (52% yield) of Boc-Ser-Asp(OBzl)-Gly-Lys(Z)-OBzl.

Melting point 57°–60° C.

$[\alpha]_D^{26}$: −23.5° (c=0.54, DMF)

Rf in thin layer chromatography [chloroform/methanol/water (8:3:1 in volume ratio)]:0.83

Elementary analysis: (for $C_{42}H_{53}N_5O_{12} \cdot 3/2H_2O$) (%)

|  | C | H | N |
|---|---|---|---|
| Calc'd: | 59.56 | 6.66 | 8.27 |
| Found: | 59.56 | 6.66 | 8.27 |

Amino acid analysis after acid decomposition: (molar ratio)

| Aspartic acid | 0.8 |
|---|---|
| Serine | 1.1 |
| Glycine | 0.8 |
| Lysine | 1.0 |

EXAMPLE 7

Preparation of Z-Asp(OBzl)-Ser-Asp(OBzl)-Gly-Lys(Z)-OBzl

To 2.17 g of the Boc-Ser-Asp(OBzl)-Gly-Lys(Z)-OBzl obtained in Example 6 were added 1.5 ml of anisole and 15 ml of TFA to give a solution. The solution was stirred at room temperature for one hour to eliminate the group Boc. To the solution was added 80 ml of an ether/petroleum ether mixture (1:1 in volume ratio) to precipitate H-Ser-Asp(OBzl)-Gly-Lys(Z)-OBzl·TFA. The precipitates were dried by suction in a desiccator containing sodium hydroxide.

Separately, 1.04 g of Z-Asp(OBzl)-OH (manufactured by Kokusan Kagaku), 0.43 g of HOBt and 0.66 g of DCC were dissolved in 10 ml of DMF. The solution was stirred under cooling with ice for 3 hours, to which was then added a solution of the above-obtained H-Ser-Asp(OBzl)-Gly-Lys(Z)-OBzl·TFA in 10 ml of DMF containing 0.41 ml of triethylamine. The mixture was stirred overnight at 4° C.

Dicyclohexylurea was removed by filtration followed by addition of 300 ml of ethyl acetate. The mixture was washed successively with saturated aqueous sodium chloride, 8% by weight aqueous Na$_2$CO$_3$, saturated aqueous sodium chloride, 0.1N HCl and saturated sodium chloride. The ethyl acetate layer was dried over anhydrous sodium sulfate, and the solvent distilled off. The residue was precipitated from petroleum ether and further reprecipitated from ethyl acetate/petroleum ether to give 0.85 g (31% yield) of Z-Asp(OBzl)-Ser-Asp(OBzl)-Gly-Lys(Z)-OBzl.

Melting point: 58° (c=0.90, DMF)

Rf in thin layer chromatography [chloroform/methanol/water (8:3:1 in volume ratio)]: 0.63

Elementary analysis: (for $C_{56}H_{62}N_6O_{15} \cdot H_2O$) (%)

|  | C | H | N |
|---|---|---|---|
| Calc'd: | 62.44 | 5.99 | 7.80 |
| Found: | 62.01 | 5.69 | 7.81 |

Amino acid analysis after acid decomposition: (molar ratio)

| Aspartic acid | 2.1 |
|---|---|
| Serine | 1.0 |
| Glycine | 0.7 |
| Lysine | 0.9 |

EXAMPLE 8

Preparation of H-Asp-Ser-Asp-Gly-Lys-OH

To a solution of 400 mg of the Z-Asp(OBzl)-Ser-Asp(OBzl)-Gly-Lys(Z)-OBzl in 20 ml of methanol, 8 ml of acetic acid and 12 ml of water was added 600 mg of 5% Pd-carbon. Into the mixture was introduced hydrogen gas for 6 hours to eliminate all of the protective groups. The Pd-carbon was removed by filtration, and water added to the filtrate. The solvents were distilled off under reduced pressure, and the residue washed with ether. Water was again added to the residue, and the mixture concentrated under reduced pressure to a volume of approximately 2 ml. The concentrate was placed on a Sephadex G-10 column (manufactured by Pharmacia, 2.5×42 cm) and developed with a 0.5% by weight aqueous solution of acetic acid. Fractions each 4 ml in volume were collected, of which fractions 20-26 showed a single peak. The fractions were pooled and freeze-dried to give 103.6 mg (52.3% yield) of the pentapeptide H-Asp-Ser-Asp-Gly-Lys-OH.

$[\alpha]_D^{26}: -18.6°$ (c=0.16, $H_2O$)

Rf in thin layer chromatography [n-butanol/pyridine/acetic acid/water (1:1:1:1 in volume ratio)]: 0.49

Rf in high performance liquid chromatography: FIG. 3

Elementary analysis: (for $C_{19}H_{32}N_6O_{11} \cdot \frac{1}{2}CH_3COOH \cdot 3H_2O$) (%)

|  | C | H | N |
|---|---|---|---|
| Calc'd: | 38.71 | 6.69 | 13.95 |
| Found: | 39.32 | 6.26 | 13.50 |

Amino acid analysis after acid decomposition: (molar ratio)

| Aspartic acid | 2.2 |
|---|---|
| Serine | 1.0 |
| Glycine | 0.7 |
| Lysine | 0.9 |

EXAMPLE 9

Preparation of Boc-Asp(OBzl)-Ser-Asp(OBzl)-Gly-Lys-OH

To 1.31 g of the Boc-Ser-Asp(OBzl)-Gly-Lys(Z)-OBzl obtained in Example 6 were added 1.21 ml of anisole and 12 ml of TFA to give a solution. The solution was stirred at room temperature for one hour to eliminate the group Boc. To the solution was added 100 ml of an ether/petroleum ether mixture (1:1 in volume ratio) to precipitate H-Ser-Asp(OBzl)-Gly-Lys(Z)-OBzl TFA. The precipitates were dried by suction in a desiccator containing sodium hydroxide.

Separately, 0.6 g of Boc-Asp(OBzl)-OH (manufactured by Kokusan Kagaku), 0.27 g of HOBt and 0.41 g of DCC were dissolved in 10 ml of DMF. The solution was stirred under cooling with ice for 3 hours, to which was then added a solution of the above-obtained H-Ser-Asp(OBzl)-Gly-Lys(Z)-OBzl TFA in 10 ml of DMF containing 0.27 ml of triethylamine. The mixture was stirred overnight at 4° C.

Dicyclohexylurea was removed by filtration followed by addition of 100 ml of ethyl acetate. The mixture was washed successively with saturated aqueous sodium chloride, 8% by weight aqueous $Na_2CO_3$, saturated aqueous sodium chloride, 8% by weight citric acid and water. The ethyl acetate layer was dried over anhydrous sodium sulfate, and the solvent distilled off. The residue was precipitated from petroleum ether and further reprecipitated from ethyl acetate/petroleum ether to give 0.75 g (45.6% yield) of Boc-Asp(OBzl)-Ser-Asp(OBzl)-Gly-Lys(Z)-OBzl.

Melting point: 49°-51° C.

$[\alpha]_D^{26}: -22.0°$ (c=0.75, DMF)

Rf in thin layer chromatography [chloroform/methanol/water (8:3:1 in volume ratio)]: 0.78

Elementary analysis: (for $C_{53}H_{64}N_6O_{15} \cdot 2H_2O$) (%)

|  | C | H | N |
|---|---|---|---|
| Calc'd: | 59.99 | 6.59 | 7.92 |
| Found: | 59.73 | 6.28 | 8.66 |

Amino acid analysis after acid decomposition: (molar ratio)

| Aspartic acid | 2.2 |
|---|---|
| Serine | 1.0 |
| Glycine | 0.7 |
| Lysine | 0.9 |

EXAMPLE 10

Preparation of Z-Ala-Asp(OBzl)-Ser-Asp(OBzl)-Gly-Lys(Z)-OBzl

To 0.4 g of the Boc-Asp(OBzl)-Ser-Asp(OBzl)-Gly-Lys(Z)-OBzl were added 0.8 ml of anisole and 8 ml of TFA to give a solution. The solution was stirred at room temperature for one hour to eliminate the group Boc. To the solution was added 80 ml of an ether/petroleum ether mixture (1:1 in volume ratio) to precipitate H-Asp(OBzl)-Ser-Asp(OBzl)-Gly-Lys(Z)-OBzl·TFA. The precipitates were dried by suction in a desiccator containing sodium hydroxide.

Separately, 0.21 g of Z-Ala-OH (manufactured by Kokusan Kagaku), 0.16 g of HOBt and 0.25 g of DCC were dissolved in 3 ml of DMF. The solution was stirred under cooling with ice for 3 hours, to which was then added a solution of the above-obtained H-Asp(OBzl)-Ser-Asp(OBzl)-Gly-Lys(Z)-OBzl·TFA in 10 ml of DMF containing 0.07 ml of triethylamine. The mixture was stirred overnight at 4° C.

Dicyclohexylurea was removed by filtration followed by addition of 100 ml of ethyl acetate. The mixture was washed successively with saturated aqueous sodium chloride, 8% by weight aqueous $Na_2CO_3$, saturated aqueous sodium chloride, 0.1N HCl and water. The ethyl acetate layer was dried over anhydrous sodium sulfate, and the solvent distilled off. The residue was precipitated from petroleum ether and further reprecipitated from ethyl acetate/petroleum ether to give 0.28 g (63.6% yield) of Z-Ala-Asp(OBzl)-Ser-Asp(OBzl)-Gly-Lys(Z)-OBzl.

Melting point: 59°-60° C.

$[\alpha]_D^{26}: -23.0°$ (c=0.79, DMF)

Rf in thin layer chromatography [chloroform/methanol/water (8:3:1 in volume ratio)]: 0.80

Elementary analysis: (for $C_{59}H_{67}N_7O_{16} \cdot \frac{1}{2}H_2O$) (%)

|  | C | H | N |
|---|---|---|---|
| Calc'd: | 62.20 | 6.01 | 8.61 |
| Found: | 62.64 | 6.70 | 9.50 |

Amino acid analysis after acid decomposition: (molar ratio)

| Aspartic acid | 2.0 |
|---|---|
| Serine | 0.9 |
| Glycine | 0.7 |
| Alanine | 1.1 |
| Lysine | 0.9 |

EXAMPLE 11

Preparation of H-Ala-Asp-Ser-Gly-Lys-OH

To a solution of 150 mg of the Z-Ala-Asp(OBzl)-Ser-Asp(OBzl)-Gly-Lys(Z)-OBzl in 10 ml of methanol, 4 ml of acetic acid and 6 ml of water was added 400 mg of 5% Pd-carbon. Into the mixture was introduced hydrogen gas for 5 hours to eliminate all of the protective groups. The Pd-carbon was removed by filtration, and water added to the filtrate. The solvents were distilled off under reduced pressure, and the residue washed with ether. Water was again added to the residue, and the mixture concentrated under reduced pressure to a volume of approximately 2 ml. The concentrate was placed on a Sephadex G-10 column (manufactured by Pharmacia, 2.5×42 cm) and developed with a 0.5% by weight aqueous solution of acetic acid. Fractions each 4 ml in volume were collected, of which fractions 21-27 showed a single peak. The fractions were pooled and freeze-dried to give 28.2 mg (40% yield) of the hexapeptide H-Ala-Asp-Ser-Asp-Gly-Lys-OH.

$[\alpha]_D^{26}$: −35.0° (c=0.16, H$_2$O)

Rf in thin layer chromatography [n-butanol/pyridine/acetic acid/water (1:1:1:1 in volume ratio)]: 0.50

Figure 4:
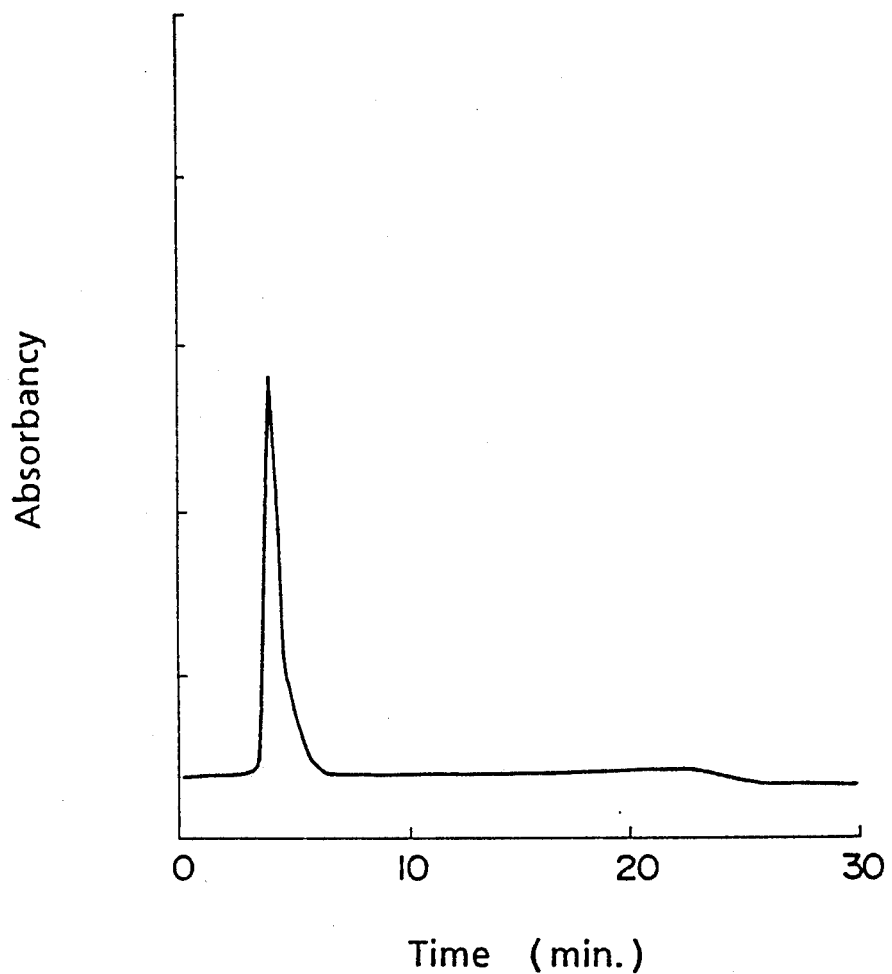
FIG. 4 shows a high performance liquid chromatogram of the peptide H-Ala-Asp-Ser-Asp-Gly-Lys-OH of the invention.

High performance liquid chromatography: FIG. 4

Elementary analysis: (for $C_{22}H_{37}N_7O_{12} \cdot 2CH_3COOH \cdot 7H_2O$) (%)

|  | C | H | N |
|---|---|---|---|
| Calc'd: | 37.63 | 7.17 | 11.81 |
| Found: | 37.08 | 6.20 | 11.88 |

Amino acid analysis after acid decomposition: (molar ratio)

| Aspartic acid | 2.2 |
|---|---|
| Serine | 0.8 |
| Glycine | 0.7 |
| Alanine | 1.1 |
| Lysine | 0.8 |

Experimental Examples

In the pharmacological experimental examples below it will be described that the peptides represented by H-Asp-Gly-Lys-OH, H-Ser-Asp-Gly-Lys-OH and H-Ala-Asp-Ser-Asp-Gly-Lys-OH have inhibitory activities on IgE antibody production as well as on histamine release and can be used as an antiallergic agent, also that the peptides represented by H-Asp-Gly-Lys-OH, H-Ser-Asp-Gly-Lys-OH, H-Asp-Ser-Asp-Gly-Lys-OH and H-Ala-Asp-Ser-Asp-Gly-Lys-OH have a vasodilating activity and can be used in therapy of diseases such as heart failure and hypertension, and further that these peptides have an inhibitory action on the activation of lymphocytes stimulated with a mitogen to enhance the productivity of humoral factors such as interleukin (IL)-1, IL-6 and TNF and can also be used as an immunoregulator useful for the therapy of autoimmune diseases such as chronic articular rheumatism and systemic lupus erythematotus.

EXPERIMENTAL EXAMPLE 1

Inhibitory activity on histamine release of H-Asp-Gly-Lys-OH, H-Ser-Asp-Gly-Lys-OH and H-Ala-Asp-Ser-Asp-Gly-Lys-OH Male Wistar rats weighing 300–350 g were passively sensitized, and intraperitoneal mast cells of the rats were employed for the test. Rat antiserum used in the passive sensitization was prepared in accordance with the method of Mota [Immunology, 7, p. 681 (1964)] and the method of Hamaoka [J. Immunology, 113, p. 958 (1974)]. Male Wistar rats (weighing 200–250 g) each were injected ovalbumin (10 mg/kg) in a volume of 5 ml/kg intramuscularly on both thighs and simultaneously 2×10 cells of killed Bordetella pertussis were intraperitoneally administered to immunize the animal. Blood was drawn from the animal under ether anesthesia via the abdominal aorta on day 12 of the initial sensitization, from which antiserum was separated. The antiserum was lyophilized and stored at −20° C. Titer of the antiserum was assayed by the 48-hour rat PCA reaction. The antiserum that showed a 128–256 fold increase in titer was used in the experiment. The antialbumin IgE serum of the rat was two fold diluted, and 1 ml of the diluted serum was intraperitoneally administered to sensitize the animal. The rat was killed by blooding 48 hours after the sensitization, and 15 ml of a phosphate buffered saline (NaCl 8 g, KCl 0.2 g, Na$_2$HPO$_4 \cdot 12H_2O$ 2.88 g, KH$_2$PO$_4$ 0.2 g, EDTA 2Na 0.2 g and bovine serum albumin 1 g, dissolved in purified water to make 1 liter, pH 7.4 (called PBS(−) hereinbelow) was intraperitoneally injected. The rat was then given light abdominal massage for about 2 min. and subjected to laparotomy to collect cells in the abdominal cavity. The cell suspension was centrifuged (1,000 rpm, 10 min.) and then resuspended in PBS(−). The PBS(−) suspension was overlayered on gum arabic density (specific gravity 1.075) followed by centrifugal separation (2,500 rpm, 10 min.). Deposited cells were washed with PBS(−) and suspended in fresh PBS(+)[a solution in which the EDTA 2Na in PBS(−) is replaced by 0.1 g of CaCl$_2$, called PBS(+)] and adjusted to 1×10$^5$ cells/ml. The cell suspension was divided into silicone-treated test tubes in a volume of 0.8 ml/tube, which were then preincubated at 37° C. for 10 min. In the cell suspension-containing test tube was placed 0.1 ml of a test solution from various solutions diluted with PBS(+) followed by incubation at 37° C. for 15 min. To the test tube was then added 0.1 ml of a mixed solution of ovalbumin antigen (final concentration 1 mg/ml) and phosphatidyl-L-serine (final concentration 100 μm/ml) followed by incubation for additional 15 min. to release histamine. For cromoglycate, one of the comparative drugs, the drug was added 30 sec. prior to the addition of the antigen, and incubation was then made for additional 15 min. The reaction was terminated by addition of 1 ml of ice-cooled PBS(+), and the reaction mixture was centrifuged at 2,500 rpm for 10 min. To 2 ml of the supernatant was added 1 ml of a 4% solution of perchloric acid, and the mixture was assayed for free histamine. For the assay of total histamine, a sample was prepared by placing 0.8 ml of a suspension of untreated mast cells in boiling water for 10 min. followed by addition of 4% perchloric acid.

Amount of histamine in the sample was assayed by fluorimetry, and percent histamine release (%) was calculated by the equation $$\text{Percent histamine release (\%)} = \frac{\text{Amount of free histamine}}{\text{Amount of total histamine}} \times 100$$

Figure 5:
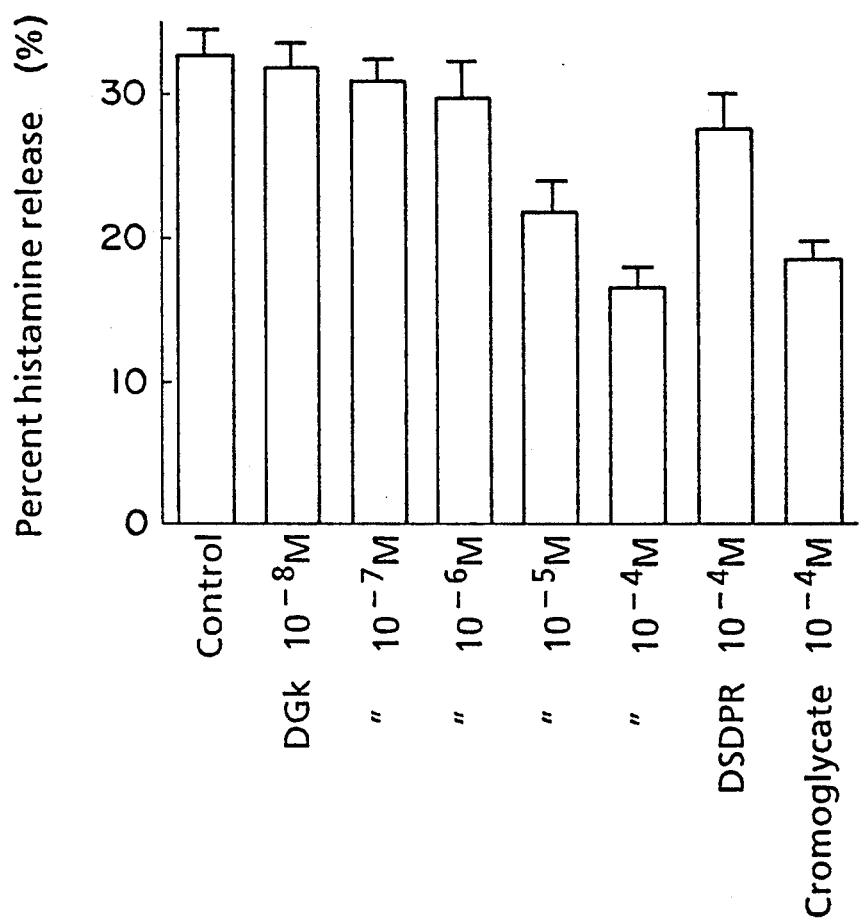
FIG. 5 is a graph indicating percent release of histamine (%) with the peptide H-Asp Gly-Lys-OH in comparison with control drugs (the peptide H-Asp-Ser-Asp-Pro-Arg-OH and cromoglycate).
Figure 6:
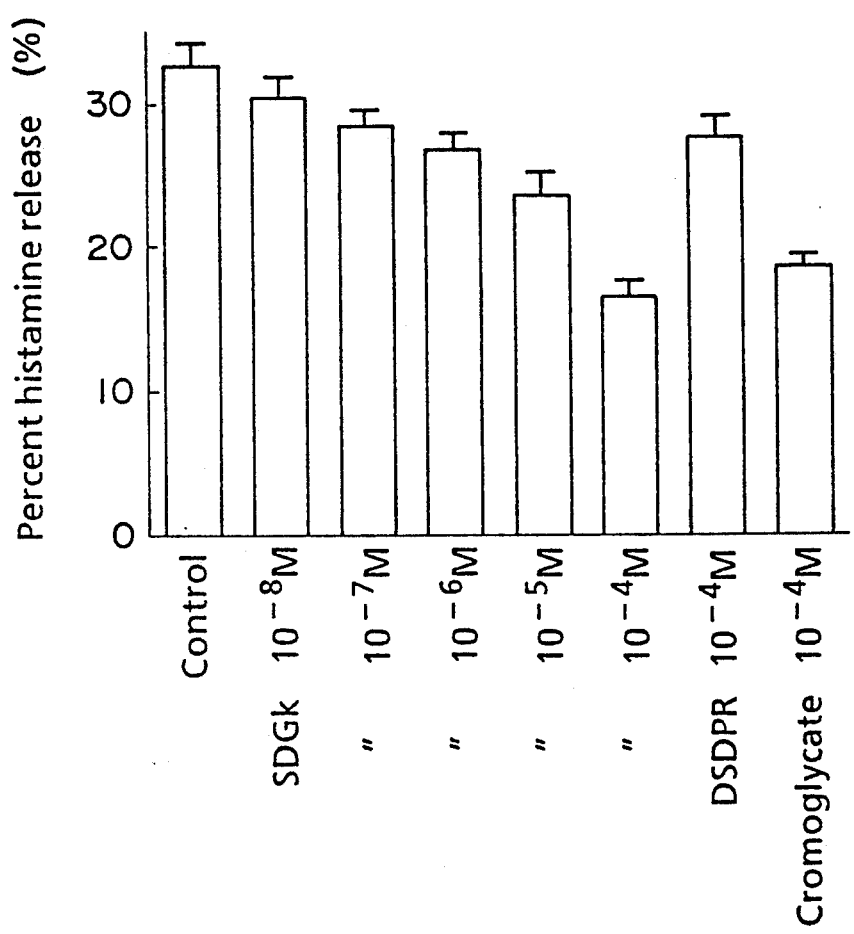
FIG. 6 is a graph indicating percent release of histamine (%) with the peptide H Ser-Asp-Gly-Lys-OH of the invention in comparison with control drugs (the peptide H-Asp-Ser-Asp-Pro-Arg-OH and cromoglycate).
Figure 7:
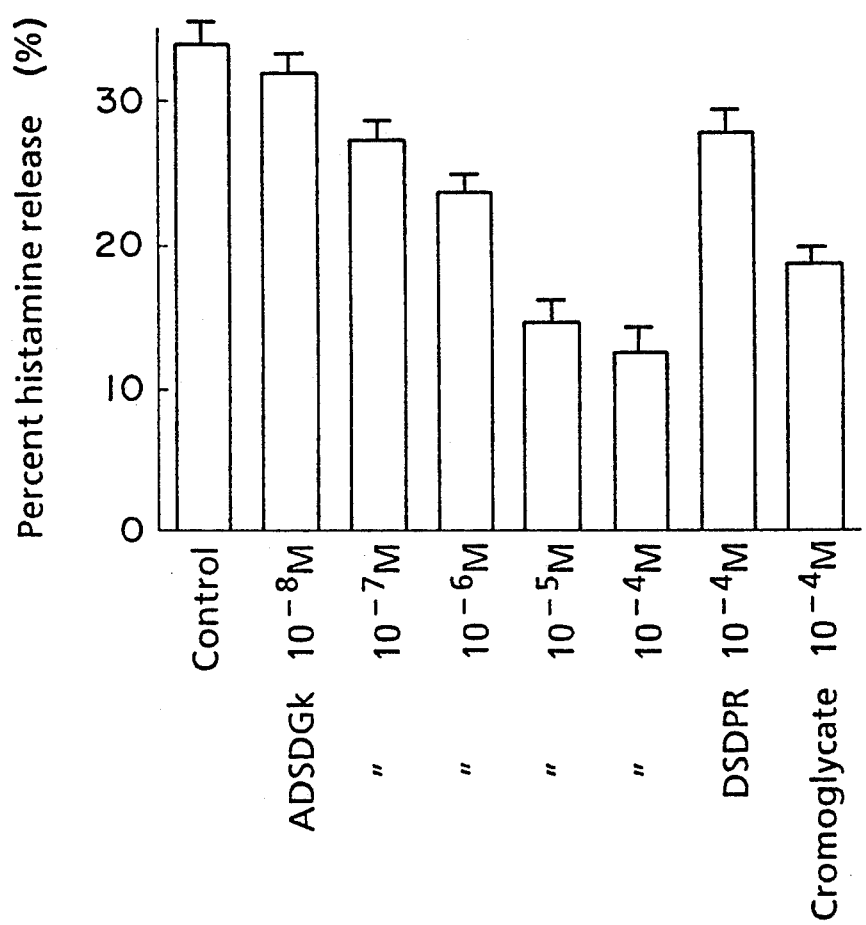
FIG. 7 is a graph indicating percent release of histamine (%) with the peptide H Ala-Asp-Ser-Asp-Gly-Lys-OH of the invention in comparison with control drugs (the peptide H-Asp Ser-Asp Pro-Arg-OH and cromoglycate).
Figure 8:
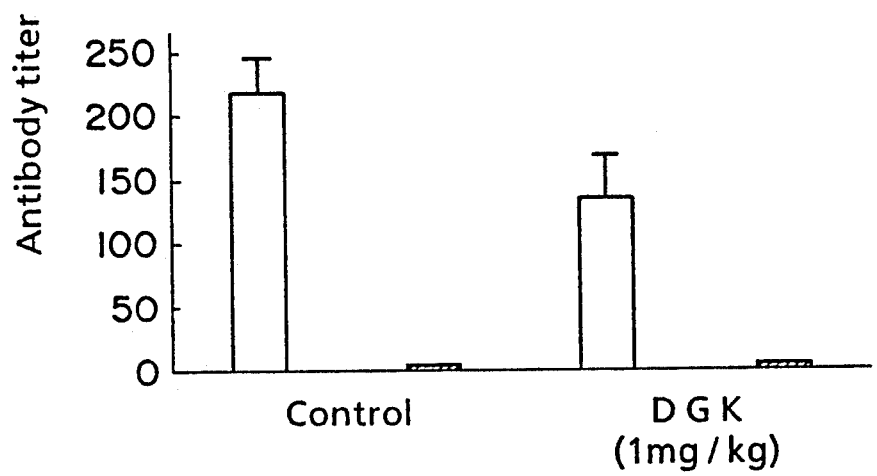
FIG. 8 is a graph indicating IgE antibody titer produced after pre-treatment with the peptide H-Asp-Gly-Lys-OH.
Figure 9:
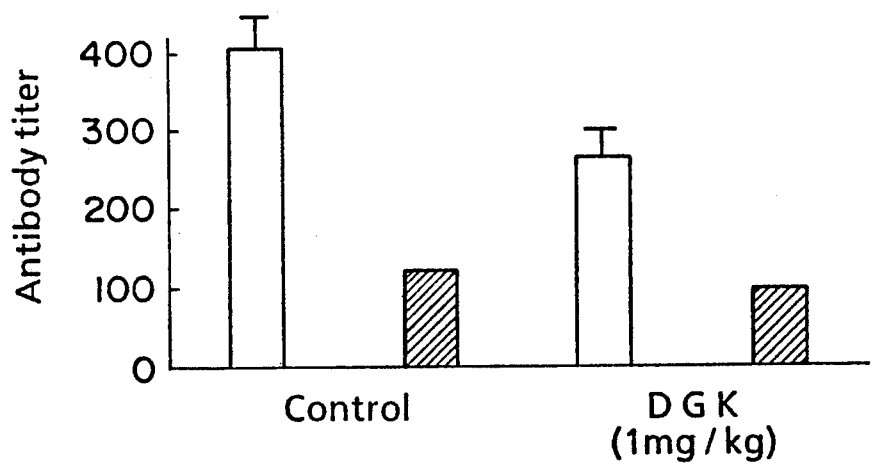
FIG. 9 is a graph indicating IgE antibody titer produced when the peptide H-Asp Gly-Lys-OH of the invention was administered during IgE antibody production.
Figure 10:
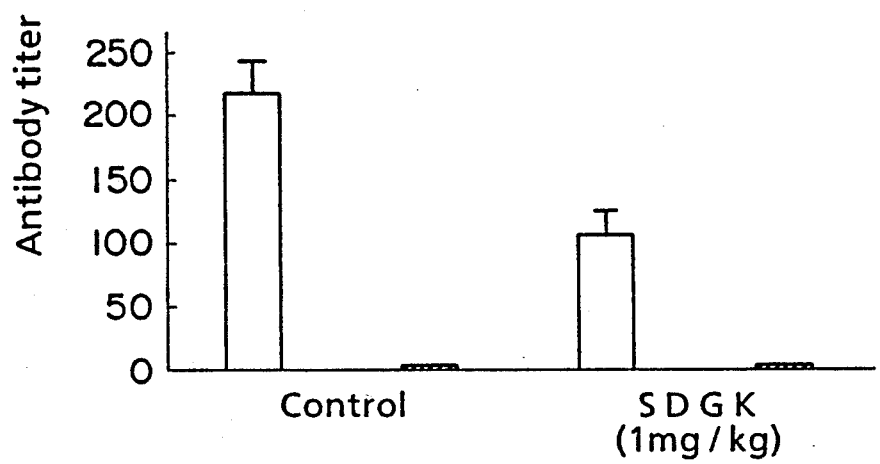
FIG. 10 is a graph indicating IgE antibody titer produced after pre-treatment with the peptide H-Ser-Asp-Gly-Lys-OH of the invention.
Figure 11:
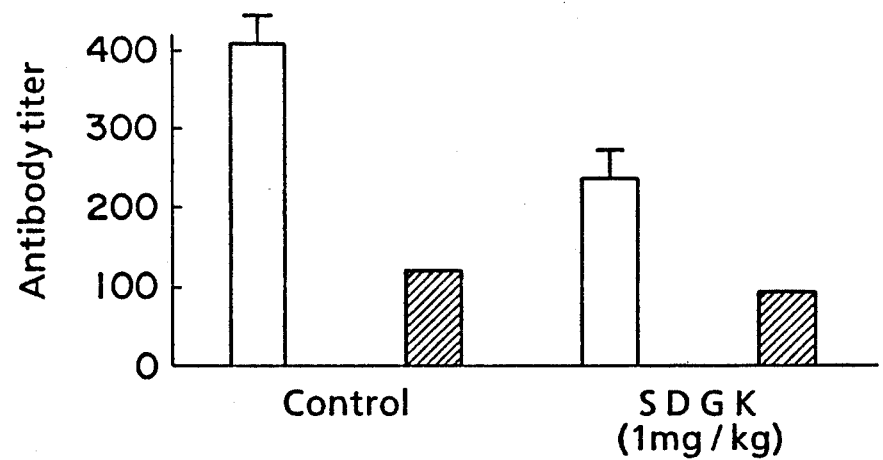
FIG. 11 is a graph indicating IgE antibody titer produced when the peptide H-Ser-Asp Gly-Lys-OH of the invention was administered during IgE antibody production.
Figure 12:
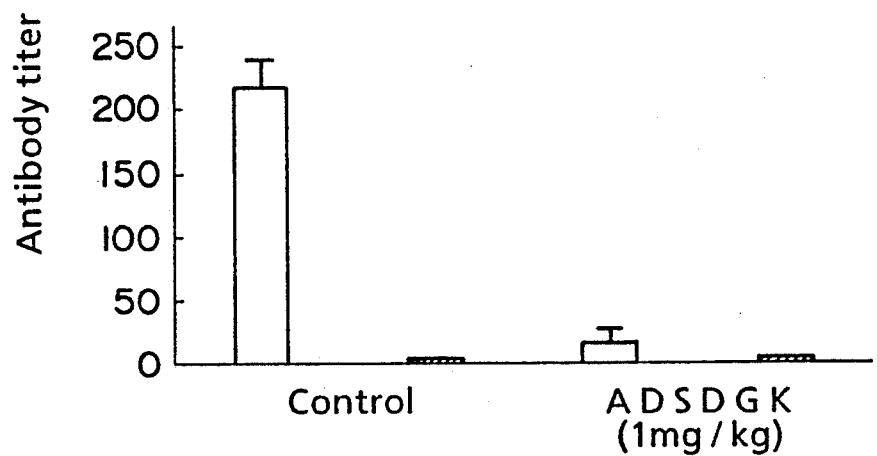
FIG. 12 is a graph indicating IgE antibody titer produced after pre-treatment with the peptide H-Ala-Asp-Ser-Asp-Gly-Lys-OH.
Figure 13:
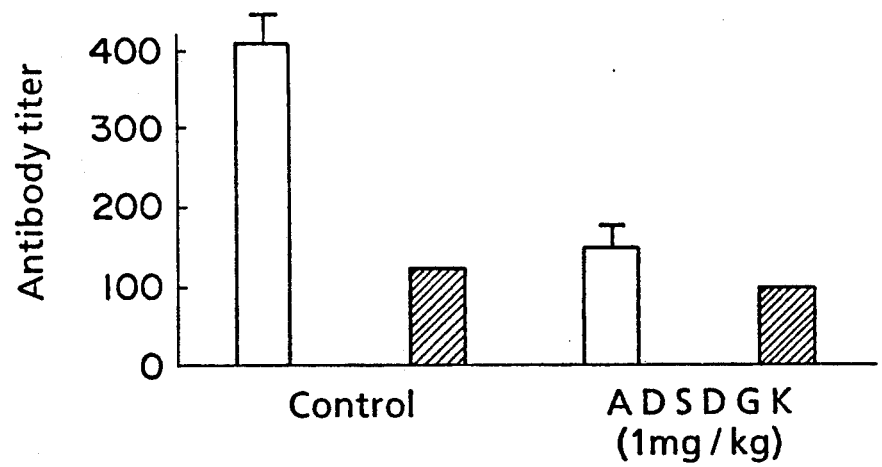
FIG. 13 is a graph indicating IgE antibody titer produced when the peptide H-Ala-Asp-Ser-Asp-Gly-Lys-OH of the invention was administered during IgE antibody production.
Figure 14:
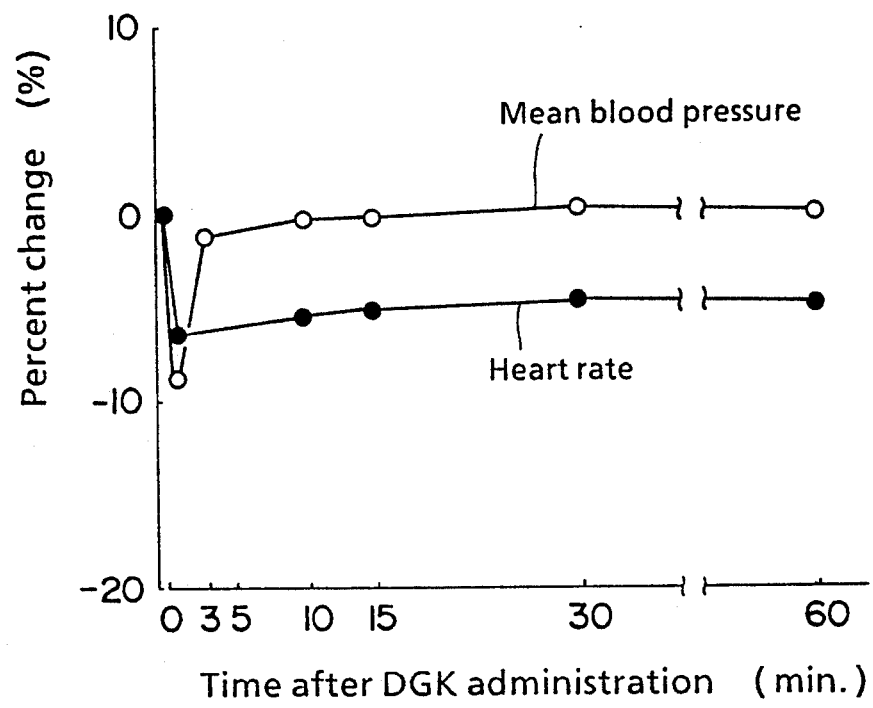
FIG. 14 is a graph indicating effects of the peptide H-Asp-Gly-Lys-OH on the circulatory system (blood pressure and heart rate).
Figure 15:
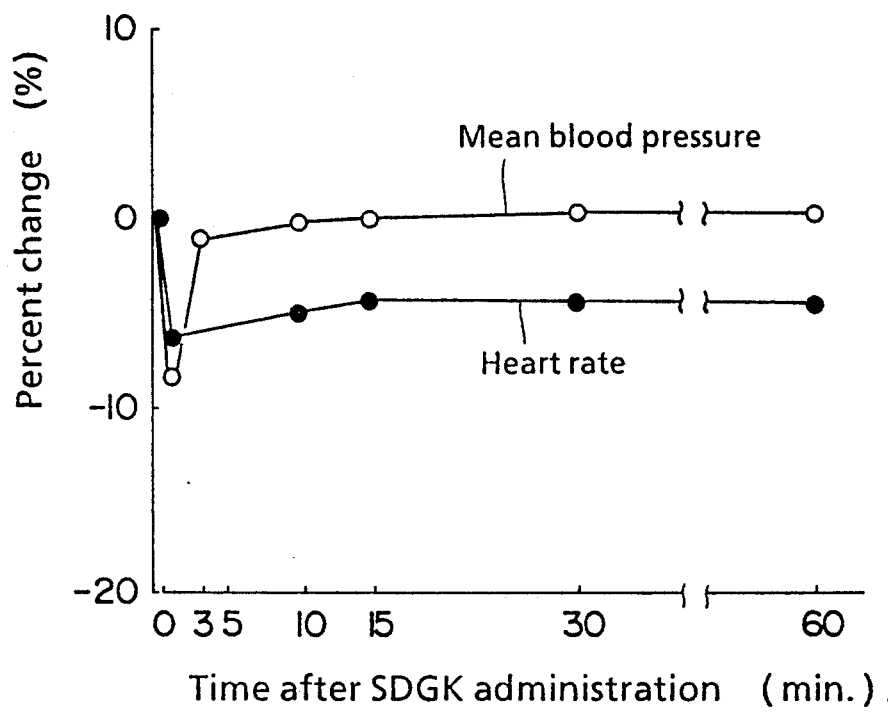
FIG. 15 is a graph indicating effects of the peptide H-Ser-Asp-Gly-Lys-OH on the circulatory system (blood pressure and heart rate).
Figure 16:
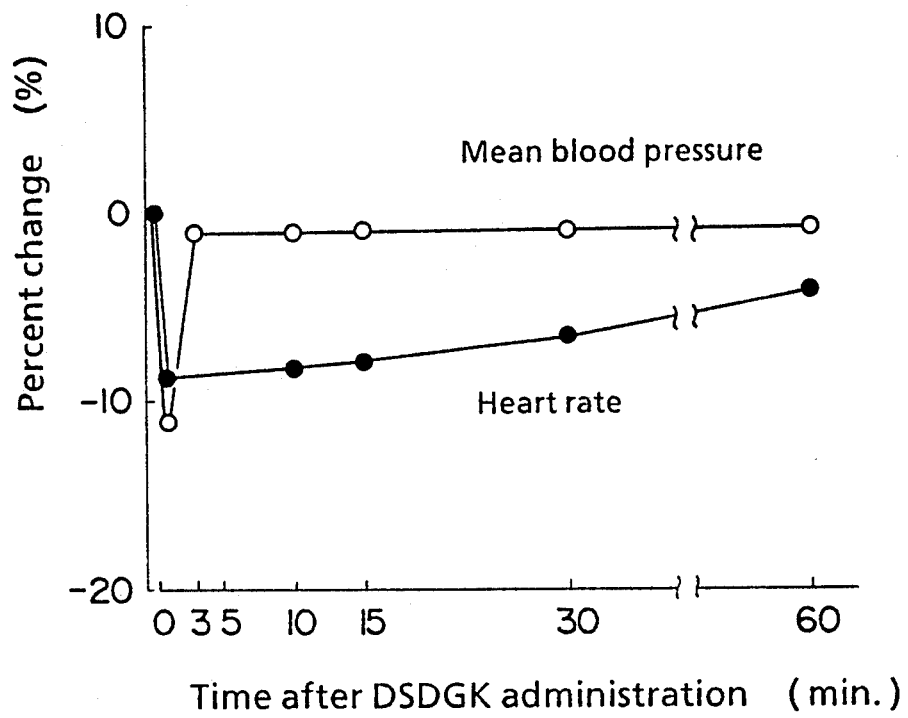
FIG. 16 is a graph indicating effects of the peptide H-Ala-Asp-Ser-Asp-Gly-Lys-OH on the circulatory system (blood pressure and heart rate).
Figure 17:
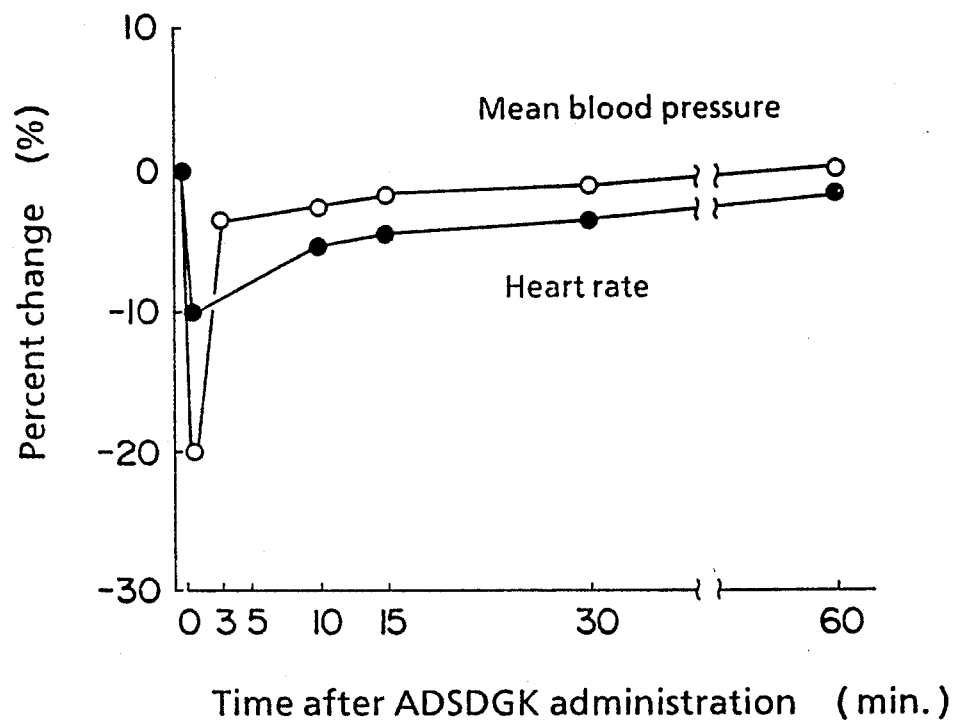

Percent histamine release (%) was shown in FIG. 5-FIG. 7 for the peptides H-Asp-Gly-Lys-OH, H-Ser-Asp-Gly-Lys-OH and H-Ala-Asp-Ser-Asp-Gly-Lys-OH and the comparative drugs. As appreciated from FIG. 5-FIG. 7 these peptides exhibited a clear inhibitory activity at a concentration of $10^5$M or higher, the potency being higher than those of the comparative drug H-Asp-Ser-Asp-Pro-Arg-OH and nearly equal to or higher than that of cromoglycate.

EXPERIMENTAL EXAMPLE 2

Inhibitory activity on IgE antibody production of H-Asp-Gly-Lys-OH, H-Ser-Asp-Gly-Lys-OH and H-Ala-Asp-Ser-Asp-Gly-Lys-OH Groups of five male BALB/c mice (6 weeks old) were used as immunized animals. Two methods of experiments were carried out using 10 μg of an antigen dinitrophenylascaris (DNP-ascaris) adsorbed on 4 mg of an immunoenhancer aluminum hydroxide gel.

In one of the experiments 1 mg of a peptide was intraperitoneally administered followed 30 min. later by intraperitoneal administration of DNP-ascaris and aluminum hydroxide gel. On day 14 blood was collected to get serum.

In the other experiment DNP-ascaris and aluminum hydroxide gel were intraperitoneally administered, and on days 7, 14 and 21, 1 mg of a peptide, H-Asp-Gly-Lys-OH, H-Ser-Asp-Gly-Lys-OH or H-Ala-Asp-Ser-Asp-Gly-Lys-OH was intraperitoneally given. Blood was collected on day 28 to get serum.

The serums obtained in the two experiments were assayed for antibody titer by the rat 48-hour PCA reaction.

Thus, male Wistar rats (200-250 g) were sensitized with the serum subcutaneously on the back, and 48 hours later a DNP-ascaris containing 0.5% Evans blue was intravenously injected via tail vein. Antibody titer was determined by measuring the pigment spot developed 30 min. later. In order to confirm that the antibody titer as obtained by the PCA reaction is an IgE antibody titer, the animal was sensitized with serum pre-treated by heating at 56° C. for 3 hours and treated in the same way as above. Antibody titer was determined by PCA reaction.

Production of IgE antibody by administration of 1 mg/kg of a peptide as determined by PCA reaction is shown in FIG. 8-FIG. 13. As apparent from FIG. 8-FIG. 13, these peptides strongly inhibited production of IgE antibody. It is noted that the antibody titer of the heat-treated serum is nearly 0 in one of the experiments (the slant-lined bar in FIGS. 8, 10 and 12), but in the other experiment antibody titer, though being slight, was shown (the slight lined bar in FIGS. 9, 11 and 13).

EXPERIMENTAL EXAMPLE 3

Vasodilating action of H-Asp-Gly-Lys-OH, H-Ser-Asp-Gly-Lys-OH, H-Asp-Ser-Asp-Gly-Lys-OH and H-Ala-Asp-Ser-Asp-Gly-Lys OH The thoracic aorta of male rabbits weighing 2.5-3 kg was excised and aortic specimens of spiral strip 25-30 mm in length were prepared. The aortic spiral strip specimens were suspended under a load of 2-g weight respectively in 10 ml of a Tyrode solution at 37°±1° C. while aerating with a mixed gas of 95% by volume oxygen and 5% by volume oxygen and maintained for 1 hour. Then, potassium chloride was added to a final concentration of 104 mM, or norepinephrine to a final concentration of $10^6$M to cause contraction of the blood vessel. The specimen was cumulatively administered with H-Asp-Gly-Lys-OH, H-Ser-Asp-Gly-Lys-OH, or H-Asp-Ser-Asp-Gly-Lys-OH or H-Ala-Asp-Ser-Asp-Gly-Lys-OH, and relaxation reaction of the blood vessel was observed. As comparative drug were employed nitroprusside (sodium salt) and verapamil.

Table 1 and Table 2 show vasodilating actions of the above-mentioned peptides and the comparative drugs in terms of percent relaxation respectively using the blood vessel contracted with potassium chloride and the contracted with norepinephrine.

It is appreciated from the data in Table 1 and Table 2 that whereas these peptides exert almost no relaxing action on the vasocontraction caused by potassium chloride, they exert a dose-dependent relaxing action on the vasocontraction caused by norepinephrine, which is similar to that of nitroprusside rather than that of verapamil.

TABLE 1

Actions of the peptides and the comparative drugs on the vasocontraction caused by potassium

| | Percent relaxation Concentration of the compound (M) | | | | |
|---|---|---|---|---|---|
| Compound | $10^{-8}$ % | $10^{-7}$ % | $10^{-6}$ % | $10^{-5}$ % | $10^{-4}$ % |
| DGK | 0 | 0 | 0 | 5.6 | 11.2 |
| DSGK | 0 | 0 | 0 | 7.2 | 18.6 |
| DSDGK | 0 | 0 | 0 | 6.6 | 19.2 |
| ADSDGK | 0 | 0 | 2.6 | 9.8 | 22.7 |
| Nitroprusside | 0 | 1.4 | 11.4 | 24.3 | 35.7 |
| Verapamil | 7.1 | 68.3 | 97.1 | 100 | 100 |

TABLE 2

Actions of the peptides and the comparative drugs on the vasocontraction caused by norepinephrine

| | Percent relaxation Concentration of the compound (M) | | | | |
|---|---|---|---|---|---|
| Compound | $10^{-8}$ % | $10^{-7}$ % | $10^{-6}$ % | $10^{-5}$ % | $10^{-4}$ % |
| DGK | 0 | 0 | 6.6 | 9.3 | 40.3 |
| DSGK | 1.7 | 9.1 | 17.7 | 25.0 | 52.6 |
| DSDGK | 2.2 | 5.1 | 7.7 | 14.1 | 58.2 |
| ADSDGK | 3.0 | 11.8 | 36.1 | 66.7 | 81.8 |
| Nitroprusside | 16.1 | 59.4 | 86.0 | 93.8 | 98.8 |
| Verapamil | 0 | 4.6 | 20.6 | 47.1 | 68.6 |

EXPERIMENTAL EXAMPLE 4

Effects of H-Asp-Gly-Lys-OH, H-Ser-Asp-Gly-Lys-OH, H-Asp-Ser-Asp-Gly-Lys-OH and H-Ala-Asp-Ser-Asp-Gly-Lys-OH on the circulatory system In order to investigate effects of the captioned peptides on the circulatory system the peptide was intravenously administered to rats to observe blood pressure, heart rate and electrocardiogram.

Wistar male rats weighing 300-350 g were anesthesized with urethane (1.5 g/kg i.v.) and subsequently measured for arterial pressure via a transducer from a canula inserted into the left femoral artery for heart rate by means of a heart rate counter using R wave of electrocardiogram (induction II) as trigger.

The peptide was administered in solution in a physiological saline solution at a dose of 30 mg per kg bodyweight of the rat via the femoral vein. FIG. 14–FIG. 17 are graphs showing blood pressure (mean blood pressure) and heart rate after administration of these peptides.

Immediately after the administration blood pressure falls and reached the lowest level (8% reduction from the mean blood pressure prior to the administration) one minute later. However, the blood pressure was recovered 3 min. after the administration to the pre-administration level. On the other hand, heart rate was reduced by 6% immediately after the administration, and the reduction continued for 60 min. In the electrocardiogram, a slight extension was observed between Q and T immediately after the administration, but the width of QRS was not changed.

EXPERIMENTAL EXAMPLE 5

Effects of the peptides H-Asp-Gly-Lys-OH, H-Ser-Asp-Gly-Lys-OH, H-Asp-Ser-Asp-Gly-Lys-OH and H-Ala-Asp-Ser-Asp-Gly-Lys-OH on the blast formation of lymphocytes stimulated with various lectins Mononuclear cells were collected by the density centrifugal method from blood of a healthy adult drawn in the presence of heparin and suspended in an RPMI-1640 culture medium (manufactured by Gibco) containing 10% by volume of bovine fetus serum (called FBS, manufactured by Dainihon Seiyaku). The suspension, adjusted to a concentration of $1 \times 10^6$ cells/ml, was divided into a 96-well Falcon microplate (manufactured by Becton Dickinson) in a volume of 100 μl/well. Then, a lectin, 1 μg/ml of PHA (phytohemagglutinin), 10 μg/ml of Con-A (concanavalin A) or 15 μg/ml of PWM (pokeweed mitogen) and one of the captioned peptides at a predetermined concentration were added followed by addition of a 10% FBS-containing RPMI-1640 medium to a final liquid volume of 200 μl. Cultivation was made in a 5% by volume $CO_2$ incubator at 37° C. for 72 hours, and 24 hours before completion of the cultivation 5 μCi of $^3$H-thymidine was added. The cells were recovered by a cell harvester (manufactured by Bio-Lab), and uptake of the $^3$H-thymidine was measured by a scintillation counter. Results of the measurement are shown in Table 3–Table 6 wherein figures indicate mean count (cpm) ± standard error.

Results shown in Table 3–Table 6 indicate that, whereas the peptides H-Asp-Gly-Lys-OH, H-Ser-Asp-Gly-Lys-OH, H-Asp-Ser-Asp-Gly-Lys-OH and H-Ala-Asp-Ser-Asp-Gly-Lys-OH produce little influence upon uptake of $^3$H-thymine by lymphocytes in the absence of a mitogen, they strongly inhibit uptake of $^3$H-thymine by the lymphocytes stimulated with a lectin, particularly with Con-A.

TABLE 3

Uptake of $^3$H-thymidine by lymphocytes stimulated with various lectines

| DGK (M) | Mitogen | |
|---|---|---|
| | None cpm | PHA (1 μg/ml) cpm |
| 0 (Control) | 1,090 (±137) | 69,600 (±4,750) |
| $10^{-8}$ | 1,120 (±202) | 62,700 (±3,380) |
| $10^{-6}$ | 925 (±202) | 62,500 (±2,120) |
| | Con-A (10 μg/ml) cpm | PWM (15 μg/ml) cpm |
| 0 (Control) | 37,800 (±1,090) | 13,600 (±2,500) |
| $10^{-8}$ | 20,000 (±1,730) | 11,500 (±1,540) |
| $10^{-6}$ | 16,700 (±1,520) | 9,590 (±538) |

TABLE 4

Uptake of $^3$H-thymidine by lymphocytes stimulated with various lectines

| SDGK (M) | Mitogen | |
|---|---|---|
| | None cpm | PHA (1 μg/ml) cpm |
| 0 (Control) | 1,090 (±137) | 69,600 (±4,750) |
| $10^{-8}$ | 1,436 (±83) | 62,100 (±2,290) |
| $10^{-6}$ | 911 (±73) | 59,000 (±3,370) |
| | Con-A (10 μg/ml) cpm | PWM (15 μg/ml) cpm |
| 0 (Control) | 37,800 (±1,090) | 13,600 (±2,500) |
| $10^{-8}$ | 24,200 (±2,200) | 10,000 (±1,530) |
| $10^{-6}$ | 24,000 (±1,730) | 9,000 (±1,690) |

TABLE 5

Uptake of $^3$H-thymidine by lymphocytes stimulated with various lectines

| DSDGK (M) | Mitogen | |
|---|---|---|
| | None cpm | PHA (1 μg/ml) cpm |
| 0 (Control) | 1,090 (±137) | 69,600 (±4,750) |
| $10^{-8}$ | 887 (±124) | 62,000 (±2,650) |
| $10^{-6}$ | 877 (±93) | 56,900 (±2,620) |
| | Con-A (10 μg/ml) cpm | PWM (15 μg/ml) cpm |
| 0 (Control) | 37,800 (±1,090) | 13,600 (±2,500) |
| $10^{-8}$ | 17,900 | 9,550 |

TABLE 5-continued

Uptake of $^3$H-thymidine by lymphocytes stimulated with various lectines

| DSDGK (M) | Mitogen | |
|---|---|---|
| | (±2,840) | (±1,340) |
| $10^{-6}$ | 19,300 | 13,000 |
| | (±4,380) | (±777) |

TABLE 6

Uptake of $^3$H-thymidine by lymphocytes stimulated with various lectines

| ADSDGK (M) | Mitogen | |
|---|---|---|
| | None cpm | PHA (1 µg/ml) cpm |
| 0 (Control) | 1,090 | 69,600 |
| | (±137) | (±4,750) |
| $10^{-8}$ | 797 | 64,100 |
| | (±175) | (±3,410) |
| $10^{-6}$ | 900 | 63,000 |
| | (±134) | (±2,420) |
| | Con-A (10 µg/ml) cpm | PWM (15 µg/ml) cpm |
| 0 (Control) | 37,800 | 13,600 |
| | (±1,090) | (±2,500) |
| $10^{-8}$ | 24,600 | 14,500 |
| | (±1,820) | (±1,550) |
| $10^{-6}$ | 21,500 | 13,600 |
| | (±1,100) | (±1,430) |

EXPERIMENTAL EXAMPLE 6

Effects of H-Asp-Gly-Lys-OH, H-Ser-Asp-Gly-Lys-OH, H-Asp-Ser-Asp-Gly-Lys-OH and H-Ala-Asp-Ser-Asp-Gly-Lys-OH on productivity of humoral factors Mononuclear cells separated by the density centrifugal method from blood of a healthy adult drawn in the presence of heparin were suspended in an RPMI-1640 culture medium containing 10% by volume of FBS. The suspension was divided into culture tubes (Falcon 2054) each at a concentration of $1 \times 10^6$ cells/ml, to which the captioned peptides were respectively added. Cultivation was made in an incubator for a week. After completion of the cultivation, the culture was centrifuged (1,500 rpm, 10 min.), and the supernatant collected and assayed for humoral factors. Interleukin 1 (IL-1) and tumor-nectrotizing factors were measured, respectively by a IL-1 radioimmunoassay kit (manufactured by Amersham International) and a TNF radioimmunoassay kit (manufactured by Medgenix). Measurement of interleukin 6 (IL-6) was made by the enzyme immunoassay method (ELISA) using IL-6 antibody (manufactured by Genzyme). Results of the measurements are shown in Table 7 wherein figures represent mean value ± standard error.

TABLE 7

Productivity of humoral factors by lymphocytes

| Additive and concentration (M) | | IL-1 (fM/ml) | IL-6 (U/ml) | TNF (pg/ml) |
|---|---|---|---|---|
| | 0 (Control) | 7.1 | 270 | 2,020 |
| | | (±0.8) | (±32) | (±125) |
| DGK | $10^{-8}$ | 7.1 | 400 | 4,110 |
| | | (±0.6) | (±29) | (±202) |
| | $10^{-6}$ | 9.5 | 440 | 4,730 |
| | | (±0.8) | (±30) | (±187) |
| SDGK | $10^{-8}$ | 10.7 | 350 | 3,620 |
| | | (±0.8) | (±20) | (±129) |
| | $10^{-6}$ | 11.2 | 280 | 4,260 |
| | | (±0.9) | (±21) | (±183) |
| DSDGK | $10^{-8}$ | 7.3 | 280 | 4,100 |
| | | (±0.9) | (±22) | (±296) |
| | $10^{-6}$ | 8.3 | 400 | 4,270 |
| | | (±0.6) | (±47) | (±271) |
| ADSDGK | $10^{-8}$ | 11.3 | 270 | 4,120 |
| | | (±0.6) | (±21) | (±192) |
| | $10^{-6}$ | 11.2 | 270 | 3,620 |
| | | (±0.9) | (±30) | (±218) |

Results shown in Table 7 indicate that H-Asp-Gly-Lys-OH, H-Ser-Asp-Gly-Lys-OH, H-Asp-Ser-Asp-Gly-Lys-OH and H-Ala-Asp-Ser-Asp-Gly-Lys-OH promote production of IL-1, IL-6 and TNF.

According to the invention there are provided the peptides H-Asp-Gly-Lys-OH, H-Ser-Asp-Gly-Lys-OH, H-Asp-Ser-Asp-Gly-Lys-OH and H-Ala-Asp-Ser-Asp-Gly-Lys-OH which are useful as a vasodilator or an immunoregulator in addition to their excellent antiallergic properties.

The peptide derivatives Z-Ser-Asp-(OBzl)-Gly-Lys(Z)-OBzl, Z-Asp(OBzl)-Ser-Asp(OBzl)-Gly-Lys(Z)-OBzl, Z-Ala-Asp(OBzl)-Ser-Asp(OBzl)-Gly-Lys(Z)-OBzl, Boc-Asp(OBzl)-Gly-Lys(Z)-OBzl, Boc-Ser-Asp(OBzl)-Gly-Lys(Z)-OBzl, and Boc-Asp(OBzl)-Ser-Asp(OBzl)-Gly-Lys(Z)-OBzl are also important intermediates for the preparation of the above-mentioned peptides, which can be prepared easily and at a low cost via these intermediate compounds.

What is claimed is:

1. An antiallergic agent comprising a tripeptide represented by the formula H-Asp-Gly-Lys-OH or a pharmaceutically acceptable salt thereof as an active ingredient.

2. An antiallergic agent comprising the tetrapeptide represented by the formula H-Ser-Asp-Gly-Lys-OH or a pharmaceutically acceptable salt thereof as an active ingredient.

3. An antiallergic agent comprising the hexapeptide represented by the formula H-Ala-Asp-Ser-Asp-Gly-Lys-OH or a pharmaceutically acceptable salt thereof as an active ingredient.

* * * * *